(12) United States Patent
He

(10) Patent No.: US 10,322,204 B2
(45) Date of Patent: Jun. 18, 2019

(54) ULTRAVIOLET STERILIZATION AND DISINFECTION DEVICE AND CONFIGURATION METHOD THEREOF

(71) Applicant: Zhiming He, Guangdong (CN)

(72) Inventor: Zhiming He, Guangdong (CN)

( * ) Notice: Subject to any disclaimer, the term of this patent is extended or adjusted under 35 U.S.C. 154(b) by 342 days.

(21) Appl. No.: 14/907,832

(22) PCT Filed: Feb. 13, 2014

(86) PCT No.: PCT/CN2014/072065
§ 371 (c)(1),
(2) Date: Jan. 27, 2016

(87) PCT Pub. No.: WO2015/043135
PCT Pub. Date: Apr. 2, 2015

(65) Prior Publication Data
US 2016/0158400 A1    Jun. 9, 2016

(30) Foreign Application Priority Data

Sep. 27, 2013 (CN) .......................... 2013 1 0451448

(51) Int. Cl.
*A61L 9/20* (2006.01)
*H01J 61/30* (2006.01)
*H01J 61/72* (2006.01)

(52) U.S. Cl.
CPC ................ *A61L 9/20* (2013.01); *H01J 61/30* (2013.01); *H01J 61/72* (2013.01)

(58) Field of Classification Search
CPC .......... A61L 9/20; A61L 2/10; A61L 2209/12; A61L 2/0047; A61L 12/063; H01J 61/72;
(Continued)

(56) References Cited

U.S. PATENT DOCUMENTS 3,617,933 A * 11/1971 Yamamoto ............ H01S 3/0326
                                                                 372/37
3,657,590 A *  4/1972 Johnson ................ H01J 61/045
                                                                 313/27
(Continued)

FOREIGN PATENT DOCUMENTS

CN            101418407 A       4/2009
CN            101634599 B       4/2011
(Continued)

OTHER PUBLICATIONS

International Search Report of PCT Patent Application No. PCT/CN2014/072065 dated Jun. 27, 2014.
(Continued)

*Primary Examiner* — Brooke Purinton

(57) ABSTRACT

Provided herein is an ultraviolet sterilization and disinfection apparatus. One or multiple low-pressure ultraviolet lamps are arranged within the ultraviolet sterilization and disinfection apparatus. A configuration method therefor is such that the inner diameters of the low-pressure ultraviolet lamps are Φ30-36 mm and the tube current density is: 0.250-0.800 A/cm2; alternatively the inner diameters are Φ26-30 mm and the tube current density is: 0.280-0.850 A/cm2; alternatively, the inner diameters are Φ20-26 mm and the tube current density is: 0.300-1.100 A/cm2; alternatively, the inner diameters are Φ15-20 mm and the tube current density is: 0.340-1.350 A/cm2. The method allows the ultraviolet dosage of the ultraviolet sterilization and disinfection apparatus to be increased, thus increasing efficiency in sterilization and disinfection.

20 Claims, 4 Drawing Sheets

(58) Field of Classification Search
CPC ... H01J 61/30; C02F 1/325; C02F 2201/3222; C02F 2201/3228; C02F 1/32; C02F 2201/3227; C02F 2201/3221
See application file for complete search history.

(56) References Cited

U.S. PATENT DOCUMENTS

| | | | | |
|---|---|---|---|---|
| 3,679,928 | A * | 7/1972 | Johnson | H01J 61/12 313/112 |
| 3,883,764 | A * | 5/1975 | Johnson | H01J 61/0672 313/577 |
| 4,835,442 | A * | 5/1989 | Sugimoto | H01J 61/28 313/17 |
| 5,170,091 | A * | 12/1992 | Wekhof | H01J 61/52 313/163 |
| 5,905,341 | A * | 5/1999 | Ikeuchi | H01J 61/822 313/636 |
| 6,552,489 | B2 * | 4/2003 | Sakakibara | C03B 23/065 313/493 |
| 2002/0159215 | A1 * | 10/2002 | Siess | B03C 3/00 361/232 |
| 2008/0152548 | A1 * | 6/2008 | Clark | A61L 9/205 422/121 |
| 2009/0004047 | A1 * | 1/2009 | Hunter | A61L 9/205 422/4 |
| 2009/0268429 | A1 * | 10/2009 | Hashimoto | C09K 11/595 362/97.1 |
| 2010/0176723 | A1 * | 7/2010 | Morimoto | H01J 61/0732 313/633 |
| 2012/0199005 | A1 * | 8/2012 | Koji | A61L 9/205 96/224 |

FOREIGN PATENT DOCUMENTS

| | | |
|---|---|---|
| CN | 102276014 A | 12/2011 |
| CN | 102284075 A | 12/2011 |
| CN | 202198887 U | 4/2012 |

OTHER PUBLICATIONS

Zhang, Yan, Development of UV Disinfection Model and Equipment Optimization, Harbin Institute of Technology Master's Degree Paper, Feb. 15, 2012, pp. 44-49, 5.2.5-5.4, the abstract.

* cited by examiner

ULTRAVIOLET STERILIZATION AND DISINFECTION DEVICE AND CONFIGURATION METHOD THEREOF

FIELD OF THE INVENTION

The present invention relates to the field of air purification techniques, and particularly to an ultraviolet sterilization and disinfection device and configuration method thereof.

BACKGROUND OF THE INVENTION

Ultraviolet sterilization and disinfection has been used in various sterilization and disinfection fields. An ultraviolet source may be an ultraviolet LED or an ultraviolet mercury vapor discharge lamp. In the field of air purification, ultraviolet may be used to inactivate harmful substances in the air, so as to improve air quality. Ultraviolet may destroy DNA and RNA of microorganisms, thus killing the microorganisms. Furthermore, ultraviolet may decompose some harmful organics, where the decomposition may be better carried out when combining with oxygenolysis effect of ozone, hydrogen peroxide and the like. Whatever type of the ultraviolet source is, ultraviolet dosage determines the ultraviolet sterilization and disinfection effect, that is, single time microorganism killing rate and single time harmful organics removing rate.

Ultraviolet dosage equals to ultraviolet illuminance multiply irradiation duration. Theoretically, each of the microorganisms like bacteria and viruses within the region that is exposed to ultraviolet irradiation need to be subjected to enough dosage of ultraviolet irradiation in order to be killed. Theoretically, a low ultraviolet dosage may be used to effect sterilization and disinfection, combing with prolonged irradiation duration. Although this method is easy to carry out, it has intrinsic drawbacks. In order to prolong the ultraviolet irradiation duration, it is generally required to increase the area or volume of the region to be sterilized by ultraviolet irradiation so as to effect thorough sterilization and disinfection, which is generally impractical. In ultraviolet sterilization and disinfection, taking into account the volume and cost of the ultraviolet sterilization and disinfection device, generally low ultraviolet illuminance and short irradiation duration are used, and irradiation times are increased through circulated irradiation. This is very low in efficiency.

As to the ultraviolet sterilization and disinfection device within the air pipes of the existing air purifier and central air-conditioner, conventional mercury vapor discharge ultraviolet lamp with power of 4 W (watt), 8 W, 15 W, 20 W, 30 W or 40 W is used. On the one hand, current or power density and thus ultraviolet illuminance are low. On the other hand, no ultraviolet sterilization and disinfection chamber is provided, thus the time that air passes the ultraviolet sterilization and disinfection region is short, and the actual ultraviolet dosage is far less than required. As compensation, the process is performed many times, and filtration is also used. However, single time microorganism killing rate is low, and risk still prevails when it comes to highly infectious and highly pathogenic bacteria and viruses. Take a commercially available small air purifier provided with ultraviolet sterilization and disinfection for example, a small ultraviolet lamp with an outer diameter of 15 mm and power of 4 W is used combined with photocatalyst, the inner face of the sterilization and disinfection chamber is coated with titanium dioxide, and the wind speed is 1.5 m/s. It turns out that, ultraviolet dosage is far less than 1 mJ/$cm^2$, photocatalyst cannot kill the bacteria efficiently, and thus the whole system cannot achieve a good sterilization and disinfection function. Taking hand-push medical sterilization and disinfection cart as another example, the sterilization and disinfection chamber is a cuboid chamber, the length, the width and the height of which are 60 cm, 40 cm and 10 cm, respectively. Three H-shaped ultraviolet lamps are used, disposed in parallel. The ultraviolet lamps have a diameter of 19 mm, an output power of 40 W and a wind speed of 2.0 m/s. The marginal minimum illuminance is 5 mW/$cm^2$, the average ultraviolet dosage is 0.3 mJ/$cm^2$ (mWs/$cm^2$) and the flow rate is 0.48 $m^3$/s. Reference dosage is 5 mJ/$cm^2$ (mWs/$cm^2$), and reference flow rate is 10 $m^3$/h (0.00278 $m^3$/s). In prior art, in order to obtain the reference dosage of 5 mJ/$cm^2$, the ratio of the volume of the ultraviolet sterilization and disinfection chamber to the flow rate (per sec) should be 0.83. And in the case of the reference flow rate of 10 $m^3$/h, in order to obtain the reference dosage of 5 mJ/$cm^2$, it is required that the output power of the ultraviolet lamp should be 23.2 W.

For an existing ultraviolet air disinfection device, the design is simple, ultraviolet dosage is far less than required, single time sterilization and disinfection efficiency is low, and therefore the overall sterilization and disinfection efficiency is undesirable. Also for a conventional ultraviolet lamp, the tube current density is less than 0.2 A/$cm^3$ and ultraviolet illuminance around the lamp is low. In order to achieve the ultraviolet dosage capable of killing microorganisms, it is required to use a large number of ultraviolet lamp and very long ultraviolet sterilization and disinfection chambers. Under this condition, if it is to increase the ultraviolet dosage and single time sterilization and disinfection efficiency, on one hand the device would be bulky and expensive and thus inconvenient to deploy. On the other hand, with heat conduction of gas flow, a conventional ultraviolet lamp with a standard wavelength of 253.7 nm decreases significantly in power efficiency, with significant power loss. The value V/(JQ) which equals to the ratio of the volume V of the sterilization and disinfection chamber to the ultraviolet dosage J and flow rate Q, and the value P/(JQ) which equals to the ratio of the output power P of the ultraviolet lamp to the ultraviolet dosage J and flow rate Q are two of the most important criteria for assessing the properties of an ultraviolet sterilization and disinfection device. In prior art, for a reference dosage of 5 mJ/$cm^2$ and a reference flow rate of 10 $m^3$/h (0.00278 $m^3$/s), in order to obtain the reference dosage of 5 mJ/$cm^2$, the ratio of the volume of the ultraviolet sterilization and disinfection chamber to the flow rate (per sec) should be larger than 0.8, and in the case of the reference flow rate of 10 $m^3$/h, in order to obtain the reference dosage of 5 mJ/$cm^2$, it is required that the output power of the ultraviolet lamp should be larger than 22.0 W.

In public places, fire control facilities are often used to cope with a sudden fire. However, spread of SARS, H7N9 and other emergent and highly infectious and pathogenic microorganisms also greatly threatens public health security. In the case of intensified pollution, those microorganisms may be entrained by and spread by means of particles (PM10, PM2.5 for example) of a haze, which would pose threat to a large number of people. There is an instant need for practical and effective technical solutions and related devices to cope with the problem.

SUMMARY OF THE INVENTION

The technical problem thus to be solved by the present invention is to provide a ultraviolet sterilization and disinfection device and configuration method thereof, by which ultraviolet dosage is increased and sterilization and disinfection is performed quickly (i.e., single time killing or removing rate), while volume and cost of the ultraviolet sterilization and disinfection device is reduced and energy consumption thereof is also taken into consideration.

The sterilization and disinfection method and device of the present invention is able to reduce the concentration of microorganisms to a non-pathogenic concentration and thus ensures public health security.

In order to achieve the goal, the present invention provides an ultraviolet sterilization and disinfection device, the ultraviolet sterilization and disinfection device being provided with one or more low pressure ultraviolet lamps. As to the lamps, inner diameter is 30-36 mm and tube current density is 0.250-0.800 A/cm$^2$; inner diameter is 26-30 mm and tube current density is 0.280-0.850 A/cm$^2$; inner diameter is 20-26 mm and tube current density is 0.300-1.100 A/cm$^2$; inner diameter is 15-20 mm and tube current density is 0.340-1.350 A/cm$^2$; inner diameter is 12-15 mm and tube current density is 0.335-1.000 A/cm$^2$; inner diameter is 10-12 mm and tube current density is 0.300-1.000 A/cm$^2$; inner diameter is 8-10 mm and tube current density is 0.300-0.900 A/cm$^2$; inner diameter is 5-8 mm and tube current density is 0.250-0.800 A/cm$^2$; or inner diameter is 3-5 mm and tube current density is 0.280-0.900 A/cm$^2$.

Compared with the existing low pressure ultraviolet lamps, the tube diameter and the tube current density are optimized, thus improving ultraviolet conversion efficiency, wherein conversion efficiency of ultraviolet irradiation with a standard wavelength of 253.7 nm is also taken into consideration.

The low pressure ultraviolet lamps are electrode-containing low pressure ultraviolet lamps or electrodeless low pressure ultraviolet lamps.

The electrode-containing low pressure ultraviolet lamps comprise hot cathode low pressure ultraviolet lamps and cold cathode low pressure ultraviolet lamps. Depending on the structure of sterilization and disinfection chamber, the low pressure lamps are of U shape, Π shape, Π shape, double U shape, double Π shape, double Π shape, triple U shape, triple Π shape, triple Π shape, quadric U shape, quadric Π shape, quadric Π shape, W shape, M shape, U-H connection shape or Π-H connection shape, in order to occupy reduced space and meet requirement of ultraviolet illuminance distribution uniformity.

Depending on the structure of sterilization and disinfection chamber, the electrodeless low pressure ultraviolet lamps are of close-loop shape, like ring shape, rectangular shape, square shape and oval shape, in order to occupy reduced space and meet requirement of ultraviolet illuminance distribution uniformity.

The ultraviolet sterilization and disinfection device further comprises an adjusting module for adjusting ultraviolet dosage of the gas flow, by adjusting output power of the low pressure ultraviolet lamps. Due to the fact that ultraviolet dosage of the ultraviolet sterilization and disinfection device is adjustable, on one hand adaptation of the sterilization and disinfection device can be improved, thus ensuring a high single time killing rate for microorganisms that require high ultraviolet dosage; and on the other hand since the whole apparatus can be operated in an initial full-load state and a reduced power consumption state for normal sterilization and disinfection, the adjusting of ultraviolet dosage contributes to reduction of power consumption. Adjusting of ultraviolet dosage is achieved by low pressure ultraviolet lamps of which power is adjustable. When tube current of the lamps drops, power also drops. Further, when mercury vapor pressure is well controlled in vicinity of optimal mercury vapor pressure, ultraviolet conversion efficiency of lamps with wavelength of 253.7 nm would not drop and will somewhat rise at times. Selection of tube current density and control of mercury vapor pressure are two key factors, and there are upper and lower limits for the selection of tube current density. When current density varies, temperature of tube wall varies, and mercury vapor pressure within the lamps varies. In this case, at the upper limit or lower limit of the current density, mercury vapor pressure need to be effectively controlled and selected by optimization test.

For the ultraviolet sterilization and disinfection device, at given wind speed of 1-5 m/s, variation of tube wall temperature, mercury vapor pressure within the lamps and variation of ultraviolet output are minor, and thus ultraviolet dosage is stable. In order to achieve this function, it is necessary to balance the tube current density and control the mercury vapor pressure.

For the ultraviolet sterilization and disinfection device, when temperature is in the range of 10-35° C., for example 30° C., or 40° C., variation of ultraviolet output is minor and ultraviolet dosage is stable.

For the ultraviolet sterilization and disinfection device, ultraviolet conversion efficiency is high as ultraviolet output power is adjusted.

After optimization, the inner diameter and the tube current density of the low pressure ultraviolet lamps are set as follows: the inner diameter is 30-36 mm and the tube current density is 0.400-0.750 A/cm$^2$; the inner diameter is 26-30 mm and the tube current density is 0.450-0.800 A/cm$^2$; the inner diameter is 20-26 mm and the tube current density is 0.450-1.050 A/cm$^2$; the inner diameter is 15-20 mm and the tube current density is 0.450-1.350 A/cm$^2$; the inner diameter is 12-15 mm and the tube current density is 0.450-0.950 A/cm$^2$; the inner diameter is 10-12 mm and the tube current density is 0.400-0.950 A/cm$^2$; the inner diameter is 8-10 mm and the tube current density is 0.400-0.850 A/cm$^2$; the inner diameter is 5-8 mm and the tube current density is 0.400-0.750 A/cm$^2$; or the inner diameter is 3-5 mm and the tube current density is 0.400-0.850 A/cm$^2$.

Specifically, the settings of the low pressure ultraviolet lamps are as follows:

Inner diameter is 30-36 mm, and tube current density is selected to be within 0.450-0.500 A/cm$^2$, 0.500-0.550 A/cm$^2$, 0.550-0.600 A/cm$^2$, 0.600-0.650 A/cm$^2$, 0.650-0.700 A/cm$^2$ or 0.700-0.750 A/cm$^2$;

Inner diameter is 26-30 mm, and tube current density is selected to be within 0.350-0.400 A/cm$^2$, 0.400-0.450 A/cm$^2$, 0.450-0.500 A/cm$^2$, 0.500-0.550 A/cm$^2$, 0.550-0.600 A/cm$^2$, 0.600-0.650 A/cm$^2$, 0.650-0.700 A/cm$^2$, 0.700-0.750 A/cm$^2$ or 0.750-0.800 A/cm$^2$;

Inner diameter is 20-26 mm, and tube current density is selected to be within 0.450-0.500 A/cm$^2$, 0.500-0.550 A/cm$^2$, 0.550-0.600 A/cm$^2$, 0.600-0.650 A/cm$^2$, 0.650-0.700 A/cm$^2$, 0.700-0.750 A/cm$^2$ 0.750-0.800 A/cm$^2$, 0.800-0.850 A/cm$^2$, 0.850-0.900 A/cm$^2$, 0.900-0.950 A/cm$^2$, 0.950-1.000 A/cm$^2$ or 1.000-1.050 A/cm$^2$;

Inner diameter is 15-20 mm, and tube current density is selected to be within 0.450-0.500 A/cm$^2$, 0.500-0.550 A/cm$^2$, 0.550-0.600 A/cm$^2$, 0.600-0.650 A/cm$^2$, 0.650-0.700 A/cm$^2$, 0.700-0.750 A/cm$^2$ 0.750-0.800 A/cm$^2$, 0.800-0.850 A/cm$^2$, 0.850-0.900 A/cm$^2$, 0.900-0.950 A/cm$^2$, 0.950-1.000 A/cm$^2$, 1.000-1.050 A/cm$^2$, 1.050-1.000 A/cm$^2$, 0.950-1.100 A/cm$^2$, 1.100-1.150 A/cm$^2$, 1.150-1.200 A/cm$^2$, 1.200-1.250 A/cm$^2$ or 1.250-1.300 A/cm$^2$;

Inner diameter is 12-15 mm, and tube current density is selected to be within 0.450-0.500 A/cm², 0.500-0.550 A/cm², 0.550-0.600 A/cm², 0.600-0.650 A/cm², 0.650-0.700 A/cm², 0.700-0.750 A/cm² 0.750-0.800 A/cm², 0.800-0.850 A/cm², 0.850-0.900 A/cm² or 0.900-0.950 A/cm²;

Inner diameter is 10-12 mm, and tube current density is selected to be within 0.400-0.450 A/cm², 0.450-0.500 A/cm², 0.500-0.550 A/cm², 0.550-0.600 A/cm², 0.600-0.650 A/cm², 0.650-0.700 A/cm², 0.700-0.750 A/cm² 0.750-0.800 A/cm², 0.800-0.850 A/cm², 0.850-0.900 A/cm² or 0.900-0.950 A/cm²;

Inner diameter is 8-10 mm, and tube current density is selected to be within 0.400-0.450 A/cm², 0.450-0.500 A/cm², 0.500-0.550 A/cm², 0.550-0.600 A/cm², 0.600-0.650 A/cm², 0.650-0.700 A/cm², 0.700-0.750 A/cm², 0.750-0.800 A/cm² or 0.800-0.850 A/cm²;

Inner diameter is 5-8 mm, and tube current density is selected to be within 0.400-0.450 A/cm², 0.450-0.500 A/cm², 0.500-0.550 A/cm², 0.550-0.600 A/cm², 0.600-0.650 A/cm², 0.650-0.700 A/cm² or 0.700-0.750 A/cm²; or Inner diameter is 3-5 mm, and tube current density is selected to be within 0.400-0.450 A/cm², 0.450-0.500 A/cm², 0.500-0.550 A/cm², 0.550-0.600 A/cm², 0.600-0.650 A/cm², 0.650-0.700 A/cm² 0.700-0.750 A/cm², 0.750-0.800 A/cm² or 0.800-0.850 A/cm².

Further, in order to ensure the ultraviolet conversion efficiency, the low pressure ultraviolet lamps are set as follows:

Inner diameter is 30-36 mm, and discharge arc length of a single lamp is larger than 80 cm;

Inner diameter is 26-30 mm, and discharge arc length of a single lamp is larger than 80 cm;

Inner diameter is 20-26 mm, and discharge arc length of a single lamp is larger than 80 cm;

Inner diameter is 15-20 mm, and discharge arc length of a single lamp is larger than 60 cm;

Inner diameter is 12-15 mm, and discharge arc length of a single lamp is larger than 60 cm;

Inner diameter is 8-10 mm, and discharge arc length of a single lamp is larger than 40 cm;

Inner diameter is 5-8 mm, and discharge arc length of a single lamp is larger than 25 cm; or Inner diameter is 3-5 mm, and discharge arc length of a single lamp is larger than 15 cm.

The low pressure ultraviolet lamp comprises a discharging vessel and a discharging device for maintaining electric discharge in the discharging vessel, wherein the discharging vessel has a seal discharging space therein, the discharging space containing mercury or amalgam and a noble gas.

The material in the low pressure ultraviolet lamps used for mercury vapor pressure control is liquid mercury. Alternatively, the material in the low pressure ultraviolet lamps used for mercury vapor pressure control is an alloy containing bismuth, indium, tin and mercury or an alloy containing bismuth, plumbum, tin and mercury.

Specifically, the liquid mercury is positioned within a discharging chamber of the low pressure ultraviolet lamps.

Specifically, when temperature at the exhaust pipe of the low pressure ultraviolet lamps or connections of the low pressure ultraviolet lamps where gas does not flow through is within the ranges of 75-95° C., 85-105° C. or 95-135° C., it is the alloy containing bismuth, indium, tin and mercury that is positioned within the lamps for mercury vapor pressure control.

Specifically, when temperature at the exhaust pipe of the low pressure ultraviolet lamps or connections of the low pressure ultraviolet lamps where gas does not flow through is within the ranges of 60-90° C., 65-95° C., 65-105° C. or 70-115° C., it is the alloy containing bismuth, plumbum, tin and mercury that is positioned within the lamps for mercury vapor pressure control.

The noble gas filled in the low pressure ultraviolet lamps may be neon, preferably a mixture of neon and argon, preferably a mixture of neon and argon in which neon accounts for more than 50%, and most preferably a mixture of neon and argon in which neon accounts for more than 70%.

An embodiment of the present invention provides a configuration method of the ultraviolet sterilization and disinfection device, comprising the aforementioned optimization of the low pressure ultraviolet lamps, as well as optimization during variations of ambient conditions like temperature and wind speed and adjusting of power. The method further comprises:

presetting initial positions of the low pressure ultraviolet lamps according to the structure of the sterilization and disinfection chamber of the ultraviolet sterilization and disinfection device;

dividing ultraviolet irradiation area of said low pressure ultraviolet lamps into discrete grids, summing average illuminance value at initial position of each grid, calculating ultraviolet illuminance uniformity across said ultraviolet irradiation area, and adjusting the positions of said low pressure ultraviolet lamps according to the ultraviolet illuminance uniformity so that the ultraviolet illuminance uniformity meets design requirements;

and determining dimension, structure and tube current density of each of said low pressure ultraviolet lamps after position adjustment, according to preset ultraviolet dosage.

In the step of adjusting the positions of said low pressure ultraviolet lamps according to the ultraviolet illuminance uniformity, ANSYS or similar fluid analysis software is used to analyze flow field of the gas flow, so that the flow field is distributed uniformly.

Further, preset average illuminance value of each conjunction within said discrete grids can be obtained using the equation as follows:

$$E = \frac{P(2\alpha + \sin 2\alpha)}{2\pi^2 DL},$$

wherein, E represents ultraviolet intensity, P represents ultraviolet power, $\alpha$ represents half the angle between the conjunction of which ultraviolet intensity is to be calculated and arc length of ultraviolet lamp, L represents discharge arc length of ultraviolet lamp and D represents normal distance between ultraviolet lamp and the conjunction of which ultraviolet intensity is to be calculated.

The so-designed ultraviolet sterilization and disinfection device comprises ultraviolet sterilization and disinfection lamps, a blower, an air inlet, a sterilization and disinfection chamber, and an air outlet, the sterilization and disinfection chamber comprising a sterilization and disinfection module having at least one ultraviolet module, the ultraviolet module using the low pressure ultraviolet lamps optimized above, wherein ultraviolet illuminance and flow field are suitably designed.

Further, the sterilization and disinfection module further comprises one or more of photocatalyst, electrostatic module, filter module and ozone module.

Further, the ultraviolet sterilization and disinfection further comprises a light shielding guide plate, the light shielding guide plate being in the form of grids, each of the grids comprising a curved light shielding guide portion and a straight guide portion being straight at least in part along the direction in which air flows towards the air outlet.

Further, the light shielding guide plate is made from a metal plate, and various voltages are applied in a spaced manner on the light shielding guide plate so that the light shielding guide plate serves the function of being electrostatic.

Further, the sterilization and disinfection module comprises at least one detachable insertion structure, or the ultraviolet module, photocatalyst module, electrostatic module, filter module and ozone module can be the detachable insertion structure. The sterilization and disinfection module of the detachable insertion structure can be mounted/dismounted separately, or a number of sterilization and disinfection modules are connected by a connection and thus can be mounted/dismounted as a whole.

Specifically, the sterilization and disinfection module of the detachable insertion structure is inserted directly into a groove prefabricated in the ultraviolet sterilization and disinfection device;

Specifically, the sterilization and disinfection module of the detachable insertion structure is connected to the ultraviolet sterilization and disinfection device by movable structures like spring snap, clip snap, etc.;

Specifically, the sterilization and disinfection module of the detachable insertion structure is pressed against onto the ultraviolet sterilization and disinfection device by screws or a housing.

In the embodiments of the present invention, by means of suitably designed inner diameter and tube current density of the low pressure ultraviolet lamps, ultraviolet illuminance around the low pressure ultraviolet lamps is increased, i.e., the ultraviolet irradiation dosage experienced by gas flow when flowing through the sterilization and disinfection chamber is increased, thus significantly improving sterilization and disinfection efficiency of the device. In addition, the shape of ultraviolet irradiation area is simplified, and specific conjunction positions for setting ultraviolet lamps and corresponding ultraviolet intensity are obtained by reusing discrete and integration calculations. The calculation has taken into account the influence of each lamp, so that ultraviolet illuminance at each position is more reasonable and thus ultraviolet irradiation within the apparatus is uniform. Moreover, by analysis of flow field, it is possible to avoid occurrence of vortex and turbulence, and thus fluid flows through each section at a stable speed. Another way is calculation by means of a model or software, where low ultraviolet illuminance is assigned to low wind speed and high ultraviolet illuminance is assigned to high wind speed, and thus each part of the gas flow is exposed to nearly equal amount of ultraviolet irradiation. As a result, ultraviolet dosage and sterilization and disinfection efficiency are improved, while sterilization and disinfection chamber is decreased in size and the whole device is low in cost, wherein energy conversion efficiency and energy consumption are also taken into consideration. By means of the light shielding guide structure provide in the ultraviolet sterilization and disinfection device, it is able to avoid ultraviolet leakage and ensure safety. By means of the sterilization and disinfection module provided in the form of a detachable insertion structure, the whole device is convenient to mount, dismount and repair. Depending on different application sites, the device can be configured together with the housing to have different performances. Also, it is possible to adjust the sterilization and disinfection performance according to various needs at different times in an application site.

DETAILED DESCRIPTION OF THE EMBODIMENTS

Figure 1:
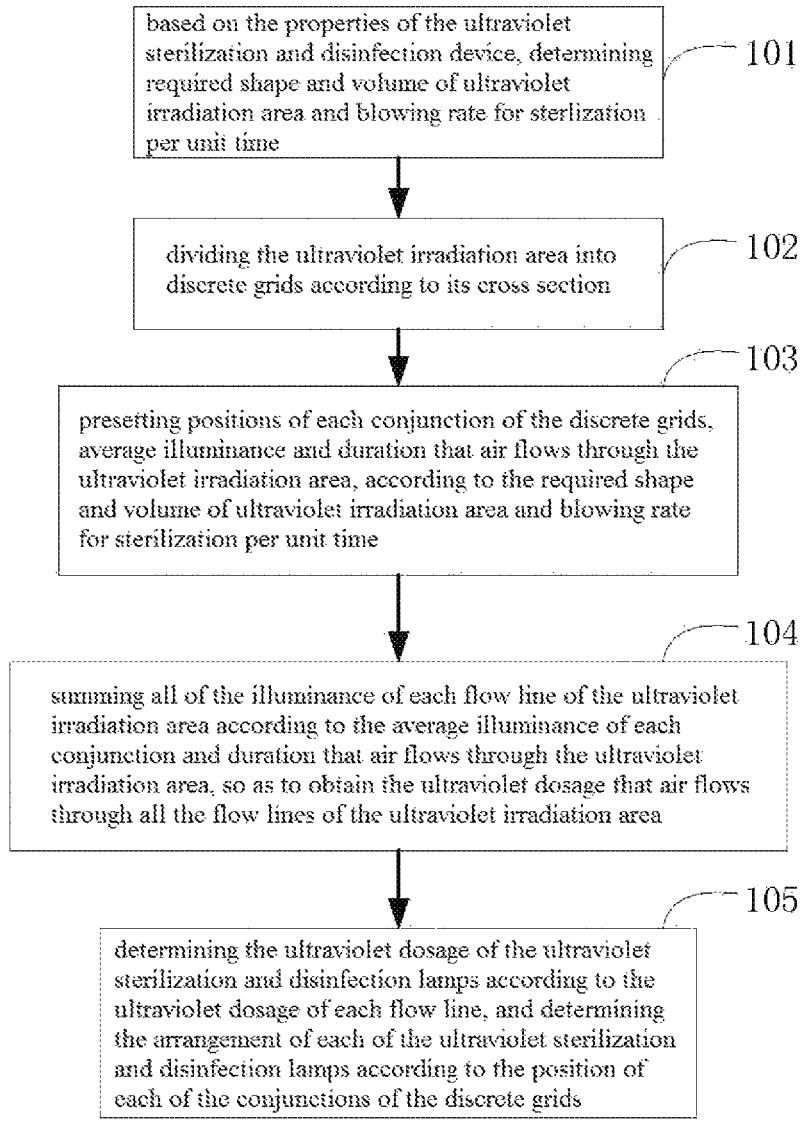
FIG. 1 is an embodiment of the configuration method of an ultraviolet sterilization and disinfection device according to the present invention.

In order to show clearly the objects, technical solutions and advantages of the present invention, the present invention is described below in more detail with reference to the drawings.

The ultraviolet sterilization and disinfection device and the configuration method thereof of the present invention provides a sterilization and disinfection device adapted for fast, safe and continuous sterilization and disinfection for human and animal activity places. The ultraviolet sterilization and disinfection device has the following advantages: 1) the ultraviolet dosage is large, and single time sterilization and disinfection efficiency is high; 2) the sterilization and disinfection chamber is smaller in volume and thus is less costly and easy to mount; 3) for an ultraviolet lamp with a standard wavelength of 253.7 nm, the ultraviolet illuminance is distributed uniformly, the output power is adjustable and general power efficiency is high; 4) sterilization and disinfection effect is reliable, irrespective of variations of wind speed, ambient temperature and the like; 5) safety is ensured, without any leakage of ultraviolet radiation; 6) the device is convenient to mount, disassemble and maintain, and its function is adjustable.

With the ultraviolet sterilization and disinfection device and configuration method thereof according to the present invention, a newly designed low pressure ultraviolet lamp is used. When calculating with a reference dosage of 5 mJ/cm$^2$ and a reference flow rate of 10 m$^3$/h (0.00278 m$^3$/s), in order to reach the reference dosage of 5 mJ/cm$^2$, the ratio of the volume of ultraviolet sterilization and disinfection chamber to flow rate per second is less than 0.8, and specifically may be less than 0.75, less than 0.70, less than 0.65, less than 0.60, less than 0.55, less than 0.50, less than 0.45, less than 0.40, less than 0.35, less than 0.30 or less than 0.25, depending on actual configuration of the devices and performance requirements thereof. With reference flow rate of 10 m$^3$/h, in order to reach the reference dosage of 5 mJ/cm$^2$, the output power required of the lamp is less than 22.0 W, and specifically may be less than 21.5 W, less than 21.0 W, less than 20.5 W, less than 20 W, less than 19.5 W, less than 19.0 W, less than 18.5 W, less than 18 W, less than 17.5 W, less than 17.0 W, less than 16.5 W, less than 16.0 W, less than 15.5 W, less than 15.0 W, less than 14.5 W or less than 14.0 W.

Reducing the volume of the ultraviolet sterilization and disinfection chamber can be realized in a few ways: 1) When the tube current density is increased, the ultraviolet illuminance within the sterilization and disinfection chamber is increased. In this case, in order to reach the target ultraviolet dosage, ultraviolet irradiation duration can be reduced, i.e. the volume is reduced; 2) Through optimization of tube current density and tube diameter, optimal match between amalgam within the lamp and the lamp itself as well as appropriate selection of lamp discharge arc length, energy conversion efficiency of ultraviolet irradiation with wavelength of 253.7 nm can be increased to some extent, contributing to the reducing of the volume; 3) With structural optimization, ultraviolet illuminance and flow field are uniformed or ultraviolet illuminance is matched with flow field, so that ultraviolet dosage is uniform at each point of the space, contributing to shortening of ultraviolet irradiation and thus reducing of volume; 4) With an ultraviolet reflection layer, ultraviolet illuminance of the sterilization and disinfection chamber can be further increased.

Reduction of energy consumption can also be realized in a few ways: 1) Although energy conversion efficiency of ultraviolet irradiation with wavelength of 253.7 nm would decrease as tube current density increases, optimal match of gases and amalgam within the lamp as well as appropriate selection of lamp discharge arc length may compensate for the decreasing, and the resultant energy conversion efficiency may be even higher as compared with ordinary ultraviolet lamp; 2) With structural optimization, ultraviolet dosage is uniform at each point of the space, and thus the required ultraviolet energy to reach certain ultraviolet dosage can be reduced; 3) With an ultraviolet reflection layer, ultraviolet utilization is improved; 4) Output power is adjusted so that energy consumption is reduced in normal sterilization and disinfection conditions, and in this case, energy conversion efficiency of ultraviolet irradiation with wavelength of 253.7 nm is increased; 5) Tube current density is increased, tube diameter is reduced, flow resistance is reduced and effective area that fluid flows across is increased, which results in increased fluid flux and correspondingly reduced power per unit of flux for given cross section of sterilization and disinfection chamber and flow rate.

The inventor has found that, reduction of the volume of sterilization and disinfection chamber of the ultraviolet sterilization and disinfection device can be realized by increasing the output power of ultraviolet lamp, i.e. increasing tube current or current density, while ensuring comparatively high ultraviolet conversion efficiency. In an embodiment of the present invention, for ultraviolet lamps with various tube diameters, different tube currents or tube current densities are designed. Furthermore, optimizations are made to filling gas within the ultraviolet lamp and mercury source, and thus ultraviolet conversion efficiency is further improved.

Specific designs and optimizations include:

Preliminary selection: 1) preliminarily selecting the filling gas of low pressure ultraviolet lamp. Among common inertial gases, xenon would not considered since it is too expensive, krypton would not be used as it decreases tube voltage and thus output power, and helium would neither be an option because it renders tube wall temperature too high and meanwhile it is difficult to choose the material for mercury pressure control. Generally, the larger the current is, the higher neon content in the selected filling gas is. As an example, the gas within the lamp is a mixture of Ar and Ne, the ratio of which is 1:1. 2) determining a mercury source, for example, liquid mercury is used. 3) determining parameters of filament, such as parameters corresponding to a maximum test current.

Testing stage: in a high-low temperature box, selecting a tube current corresponding to a current density of 0.6-0.8 A/cm$^2$, testing variations of ultraviolet illuminance and temperature of liquid mercury, and obtaining saturated mercury vapor pressure corresponding to maximum ultraviolet illuminance of various tube diameters, i.e. optimal mercury vapor pressure for each tube diameter.

Determining amalgam: 1) based on optimal mercury vapor pressures for various tube diameters, contemplating amalgam or structure of a lamp, respectively, so that the lamp exhibits a maximum ultraviolet illuminance at an ambient temperature of 20-30° C.; 2) making the lamps using three different kinds of gases, pure Ar, pure Ne, and mixture of Ar and Ne (1:1), making three groups of lamps for each tube diameter.

Further testing: in a dark room, testing ultraviolet illuminance for each lamp with different currents (by adjusting the current or changing a preset value of the ballast, calculating ultraviolet power based on ultraviolet illuminance, and then calculating ultraviolet conversion efficiency.

Further optimization: adjusting the filling gas, so that the output power and thus efficiency of the lamp at various current densities can be increased. On this basis, tube diameter, tube current density and ultraviolet conversion efficiency are finally selected.

After a large number of previous tests designed specially, optimal results are obtained in Table 1. Tests on variations of ultraviolet illuminance or temperature of amalgam are carried out using unique testing method of the present applicant (disclosed in ZL 200910041936.8), and the type of ultraviolet illuminometer is Yuanfang UZ-2000Z.

TABLE 1 ultraviolet conversion efficiency under different tube diameters and tube current densities

| inner diameter/mm | tube length/mm | tube current/A | tube current density/A/cm$^2$ | $\eta$max | filling gas | mercury source |
|---|---|---|---|---|---|---|
| 35.0 | 1554 | 0.425 | 0.044 | 49.0% | Ar (or mixture of Ar and Ne) | liquid mercury |
|  | 1554 | 0.8 | 0.083 | 46.5% |  |  |
|  | 1554 | 1.5 | 0.156 | 45.0% |  | amalgam |
|  | 1554 | 1.8 | 0.187 | 43.6% |  |  |
|  | 1554 | 2.1 | 0.218 | 41.1% |  |  |
|  | 1554 | 2.5 | 0.260 | 40.8% |  |  |
|  | 1554 | 3.2 | 0.333 | 40.1% | Ne (or mixture of Ne and Ar) |  |
|  | 1554 | 3.8 | 0.395 | 37.8% |  |  |

TABLE 1-continued ultraviolet conversion efficiency under different tube diameters and tube current densities

| inner diameter/mm | tube length/mm | tube current/A | tube current density/A/cm² | ηmax | filling gas | mercury source |
|---|---|---|---|---|---|---|
|  | 1554 | 4.5 | 0.468 | 36.7% |  |  |
|  | 1554 | 5.5 | 0.572 | 35.5% |  |  |
|  | 1554 | 6.5 | 0.676 | 33.8% |  |  |
|  | 1554 | 7.5 | 0.780 | 31.2% |  |  |
|  | 1554 | 8.5 | 0.883 | 28.6% |  |  |
| 29.0 | 1554 | 0.425 | 0.064 | 47.2% | Ar (or mixture | liquid mercury |
|  | 1554 | 1.2 | 0.182 | 43.2% | of Ne and Ar) | amalgam |
|  | 1554 | 1.5 | 0.227 | 42.3% |  |  |
|  | 1554 | 2.1 | 0.318 | 37.8% |  |  |
|  | 1554 | 2.5 | 0.378 | 36.3% | Ne (or mixture |  |
|  | 1554 | 3.2 | 0.484 | 35.6% | of Ne and Ar) |  |
|  | 1554 | 3.8 | 0.575 | 34.8% |  |  |
|  | 1554 | 4.5 | 0.681 | 33.3% |  |  |
|  | 1554 | 5.5 | 0.833 | 32.0% |  |  |
|  | 1554 | 6.5 | 0.984 | 28.2% |  |  |
| 22.0 | 1554 | 0.425 | 0.112 | 46.5% | Ar (or mixture | liquid mercury |
|  | 1554 | 0.6 | 0.158 | 45.4% | of Ne and Ar) |  |
|  | 1554 | 0.8 | 0.210 | 44.5% |  | amalgam |
|  | 1554 | 1.0 | 0.263 | 43.6% |  |  |
|  | 1554 | 1.2 | 0.316 | 41.9% |  |  |
|  | 1554 | 1.5 | 0.395 | 37.5% |  |  |
|  | 1554 | 1.8 | 0.474 | 37.0% | Ne (or mixture |  |
|  | 1554 | 2.1 | 0.552 | 36.5% | of Ne and Ar) |  |
|  | 1554 | 2.5 | 0.658 | 36.0% |  |  |
|  | 1554 | 3.2 | 0.842 | 35.0% |  |  |
|  | 1554 | 3.8 | 1.000 | 33.5% |  |  |
|  | 1554 | 4.5 | 1.184 | 30.5% |  |  |
|  | 1554 | 5.5 | 1.447 | 28.5% |  |  |
| 17.0 | 1554 | 0.33 | 0.145 | 46.8% | Ar (or mixture | liquid mercury |
|  | 1554 | 0.425 | 0.187 | 45.3% | of Ne and Ar) |  |
|  | 1554 | 0.6 | 0.264 | 42.8% |  |  |
|  | 1554 | 0.8 | 0.352 | 40.1% |  | amalgam |
|  | 1554 | 1.0 | 0.441 | 39.2% |  |  |
|  | 1554 | 1.2 | 0.529 | 38.5% | Ne (or mixture |  |
|  | 1554 | 1.5 | 0.661 | 37.9% | of Ne and Ar) |  |
|  | 1554 | 1.8 | 0.793 | 37.5% |  |  |
|  | 1554 | 2.1 | 0.925 | 36.2% |  |  |
|  | 1554 | 2.5 | 1.101 | 34.8% |  |  |
|  | 1554 | 3.2 | 1.410 | 30.9% |  |  |
| 13.6 | 1554 | 0.22 | 0.151 | 46.2% | Ar (or mixture | liquid mercury |
|  | 1554 | 0.33 | 0.227 | 43.5% | of Ne and Ar) |  |
|  | 1554 | 0.425 | 0.293 | 42.4% |  |  |
|  | 1554 | 0.6 | 0.413 | 39.3% |  | amalgam |
|  | 1554 | 0.8 | 0.551 | 37.6% |  |  |
|  | 1554 | 1 | 0.688 | 36.8% |  |  |
|  | 1554 | 1.2 | 0.826 | 35.5% |  |  |
|  | 1554 | 1.5 | 1.033 | 32.7% |  |  |
|  | 1554 | 1.8 | 1.239 | 26.6% |  |  |
|  | 1554 | 2.1 | 1.446 | 25.2% |  |  |
| 10.8 | 1146 | 0.17 | 0.186 | 43.2% | Ar (or mixture | liquid mercury |
|  | 1146 | 0.22 | 0.240 | 41.6% | of Ne and Ar) |  |
|  | 1146 | 0.33 | 0.360 | 39.5% |  | amalgam |
|  | 1146 | 0.425 | 0.464 | 38.4% |  |  |
|  | 1146 | 0.6 | 0.655 | 35.3% |  |  |
|  | 1146 | 0.8 | 0.873 | 33.7% |  |  |
|  | 1146 | 1.0 | 1.092 | 30.3% |  |  |
|  | 1146 | 1.2 | 1.310 | 27.8% |  |  |
| 9.0 | 845 | 0.17 | 0.267 | 36.0% | Ar (or mixture | liquid mercury |
|  | 845 | 0.22 | 0.346 | 34.3% | of Ne and Ar) |  |
|  | 845 | 0.33 | 0.519 | 32.1% |  | amalgam |
|  | 845 | 0.425 | 0.668 | 28.6% |  |  |
|  | 845 | 0.6 | 0.943 | 26.5% |  |  |
|  | 845 | 0.8 | 1.258 | 23.3% |  |  |
|  | 845 | 1.0 | 1.572 | 20.2% |  |  |
| 7.0 | 845 | 0.12 | 0.312 | 34% | Ar (or mixture | amalgam |
|  | 845 | 0.17 | 0.442 | 32.0% | of Ne and Ar) |  |
|  | 845 | 0.22 | 0.572 | 29.2% |  |  |
|  | 845 | 0.33 | 0.857 | 27.1% |  |  |
|  | 845 | 0.425 | 1.104 | 24.1% |  |  |
|  | 845 | 0.6 | 1.559 | 20.3% |  |  |

TABLE 1-continued ultraviolet conversion efficiency under different tube diameters and tube current densities

| inner diameter/mm | tube length/mm | tube current/A | tube current density/A/cm² | ηmax | filling gas | mercury source |
|---|---|---|---|---|---|---|
| 4.0 | 500 | 0.05 | 0.397 | 33.8% | Ar (or mixture of Ne and Ar) | amalgam |
|  | 500 | 0.08 | 0.637 | 28.3% |  |  |
|  | 500 | 0.12 | 0.955 | 25.8% |  |  |
|  | 500 | 0.17 | 1.353 | 21.8% |  |  |
|  | 500 | 0.22 | 1.751 | 18.3% |  |  | note:
tube current density = tube current/inner sectional area of the tube

An upper limit of tube current density is determined based on minimum ultraviolet conversion efficiency. From table 1, tube current density ranges corresponding to various tube diameter ranges can be preliminarily determined.

Inner diameter is 35.0 mm, and tube current density should be no larger than 0.850 A/cm², and ultraviolet conversion efficiency η should be greater than or equal to 30%. For an inner diameter between 30 mm and 36 mm, tube current density should be no larger than 0.800 A/cm², and ultraviolet conversion efficiency η should be greater than or equal to 30%.

Inner diameter is 29.0 mm, and tube current density should be no larger than 0.900 A/cm², and ultraviolet conversion efficiency η should be greater than or equal to 30%. For an inner diameter between 26 mm and 30 mm, tube current density should be no larger than 0.850 A/cm², and ultraviolet conversion efficiency η should be greater than or equal to 30%.

Inner diameter is 22.0 mm, and tube current density should be no larger than 1.150 A/cm², and ultraviolet conversion efficiency η should be greater than or equal to 30%. For an inner diameter between 20 mm and 26 mm, tube current density should be no larger than 1.100 A/cm², and ultraviolet conversion efficiency η should be greater than or equal to 30%.

Inner diameter is 17.0 mm, and tube current density should be no larger than 1.400 A/cm², and ultraviolet conversion efficiency η should be greater than or equal to 30%. For an inner diameter between 15 mm and 20 mm, tube current density should be no larger than 1.350 A/cm², and ultraviolet conversion efficiency η should be greater than or equal to 30%.

Inner diameter is 13.6 mm, and tube current density should be no larger than 1.050 A/cm², and ultraviolet conversion efficiency η should be greater than or equal to 30%. For an inner diameter between 12 mm and 15 mm, tube current density should be no larger than 1.000 A/cm², and ultraviolet conversion efficiency η should be greater than or equal to 30%.

Inner diameter is 10.8 mm, and tube current density should be no larger than 1.050 A/cm², and ultraviolet conversion efficiency η should be greater than or equal to 30%. For an inner diameter between 10 mm and 12 mm, tube current density should be no larger than 1.000 A/cm², and ultraviolet conversion efficiency η should be greater than or equal to 30%.

Inner diameter is 9.0 mm, and tube current density should be no larger than 0.950 A/cm², and ultraviolet conversion efficiency η should be greater than or equal to 25%. For an inner diameter between 8 mm and 10 mm, tube current density should be no larger than 0.900 A/cm², and ultraviolet conversion efficiency η should be greater than or equal to 25%.

Inner diameter is 7.0 mm, and tube current density should be no larger than 0.850 A/cm², and ultraviolet conversion efficiency η should be greater than or equal to 25%. For an inner diameter between 5 mm and 8 mm, tube current density should be no larger than 0.800 A/cm², and ultraviolet conversion efficiency η should be greater than or equal to 25%.

Inner diameter is 4.0 mm, and tube current density should be no larger than 0.950 A/cm², and ultraviolet conversion efficiency η should be greater than or equal to 25%. For an inner diameter between 3 mm and 5 mm, tube current density should be no larger than 0.900 A/cm², and ultraviolet conversion efficiency η should be greater than or equal to 25%.

From the optimized tube current density range concluded above, by combining the influence of heat conduction of gas flow (i.e. variation of wind speed), tube current density corresponding to each tube diameter range can be further determined (see table 2).

TABLE 2 ultraviolet conversion efficiency under different wind speeds with inner diameters of 17 mm and 13.6 mm, respectively

| inner diameter/mm | tube length/mm | tube current/A | tube current density A/cm² | wind speed m/s | ultraviolet efficiency/η | mercury source |
|---|---|---|---|---|---|---|
| 17.0 | 1554 | 2.158 | 0.951 | 0 | 9.9% | liquid mercury |
|  |  | 2.114 | 0.931 | 1.8 | 33.4% |  |
|  |  | 2.107 | 0.928 | 2.8 | 33.6% |  |
|  |  | 2.099 | 0.925 | 3.4 | 34.3% |  |
|  |  | 2.090 | 0.921 | 4.8 | 35.1% |  |
|  |  | 1.822 | 0.803 | 0 | 13.5% |  |
|  |  | 1.779 | 0.784 | 1.8 | 37.5% |  |
|  |  | 1.774 | 0.782 | 2.8 | 37.6% |  |
|  |  | 1.770 | 0.780 | 3.4 | 38.4% |  |
|  |  | 1.762 | 0.776 | 4.8 | 38.9% |  |

TABLE 2-continued ultraviolet conversion efficiency under different wind speeds
with inner diameters of 17 mm and 13.6 mm, respectively

| inner diameter/mm | tube length/mm | tube current/A | tube current density A/cm² | wind speed m/s | ultraviolet efficiency/η | mercury source |
|---|---|---|---|---|---|---|
| | | 0.980 | 0.432 | 0 | 26.1% | |
| | | 0.971 | 0.428 | 1.8 | 41.2% | |
| | | 0.971 | 0.428 | 2.8 | 40.7% | |
| | | 0.971 | 0.428 | 3.4 | 40.0% | |
| | | 0.971 | 0.428 | 4.8 | 40.6% | |
| | | 0.830 | 0.366 | 0 | 34.6% | |
| | | 0.801 | 0.353 | 1.8 | 38.6% | |
| | | 0.790 | 0.348 | 2.8 | 37.7% | |
| | | 0.775 | 0.341 | 3.4 | 37.3% | |
| | | 0.772 | 0.340 | 4.8 | 35.2% | |
| 13.6 | 1554 | 1.560 | 1.073 | 0 | 9.8% | liquid mercury |
| | | 1.510 | 1.039 | 1.8 | 34.9% | |
| | | 1.502 | 1.034 | 2.8 | 35.7% | |
| | | 1.499 | 1.032 | 3.4 | 36.3% | |
| | | 1.487 | 1.024 | 4.8 | 37.2% | |
| | | 1.089 | 0.750 | 0 | 18.6% | |
| | | 1.023 | 0.704 | 1.8 | 38.5% | |
| | | 1.001 | 0.698 | 2.8 | 38.8% | |
| | | 0.992 | 0.683 | 3.4 | 39.8% | |
| | | 0.990 | 0.682 | 4.8 | 40.4% | |
| | | 0.808 | 0.556 | 0 | 28.4% | |
| | | 0.789 | 0.543 | 1.86 | 41.0% | |
| | | 0.780 | 0.537 | 2.8 | 40.3% | |
| | | 0.778 | 0.536 | 3.4 | 39.6% | |
| | | 0.776 | 0.534 | 4.8 | 39.1% | |
| | | 0.510 | 0.351 | 0 | 36.9% | |
| | | 0.498 | 0.343 | 1.8 | 37.3% | |
| | | 0.489 | 0.337 | 2.8 | 36.7% | |
| | | 0.485 | 0.334 | 3.4 | 35.3% | |
| | | 0.483 | 0.332 | 4.8 | 34.4% | |

As to other tube diameters, similar methods can be used for tests and comparisons, which will not be explained in detail herein.

Generally, when tube current density is greater than or equal to 0.300 A/cm², temperature of tube wall of the lamp is comparatively high, and it is necessary to use amalgam for mercury vapor pressure control. The inventor has occasionally found that, at gas velocity of 1-5 m/s, when liquid mercury is used as mercury source, high ultraviolet conversion efficiency can also be ensured. This is because heat conduction of gas flow during gas sterilization and disinfection additionally produces a cold end for mercury vapor pressure control. In this case, liquid mercury is positioned within a discharge chamber of the low pressure ultraviolet lamp. In another design, amalgam is fixed at a certain position at an inner wall of the quartz tube of a low pressure ultraviolet lamp. This position is a conjunction at which the lamp is fixed, where gas does not flow through, heat conduction is poor and temperature is comparatively high. For example, the conjunction is a bridge connection of H tubes, where temperature is 60-130° C., depending on lamp current and structure and material of the connection. By using an alloy containing bismuth, indium, tin and mercury or an alloy containing bismuth, plumbum, tin and mercury, the lamp can be better adapted to the environment. At ambient temperature of 0-40° C. or variation of ambient temperature of 50° C. or 60° C., variation of ultraviolet output of the lamp is less than 10%. Thus even under harsh conditions or significant variations of environment, good sterilization and disinfection effect can be ensured.

At high wind speed and low current density, ultraviolet conversion efficiency is at its minimum, and corresponding tube current density is at its lower limit.

Specifically, when wind speed is set to be 1-3 m/s, 1.5-3.5 m/s, 2-4 m/s, 2.5-4.5 m/s, 1.5-4 m/s, 2-5 m/s or the like, it is likely to result in a higher ultraviolet conversion efficiency and better adaptation to the environment.

Accordingly, comprehensive selections can be made.

Inner diameter is 30-36 mm, and tube current density is selected to be 0.280-0.800 A/cm2, wind speed is 1-5 m/s, and ultraviolet conversion efficiency η is greater than or equal to 30%. Moreover, in order to ensure ultraviolet conversion efficiency at ambient temperature of 10-35° C., tube current density is selected to be 0.350-0.750 A/cm². In addition, in order to ensure ultraviolet conversion efficiency when lamp power is adjusted, tube current density is selected according to variation range of lamp power. In this connection, the ultraviolet sterilization and disinfection device of the present embodiment is further provided with an adjusting module, for adjusting ultraviolet output power and ultraviolet dosage of the gas flow. When tube current density is selected to be 0.400 A/cm² and drops to 0.280 A/cm², output power is dropped to 70%, i.e. the output power is adjustable to be 70%. When tube current density is selected to be 0.450 A·cm², output power is adjustable to be 62%; when tube current density is selected to be 0.500 A·cm², output power is adjustable to be 56%; when tube current density is selected to be 0.550 A·cm², output power is adjustable to be 51%; when tube current density is selected to be 0.600 A·cm², output power is adjustable to be 46%; when tube current density is selected to be 0.650 A·cm², output power is adjustable to be 43%; when tube current density is selected to be 0.700 A·cm², output power is adjustable to be 40%; and when tube current density is selected to be 0.750 A·cm², output power is adjustable to be 37%. In order to ensure ultraviolet conversion efficiency when output power is adjusted, according to variation range of output power, tube current density is selected to be within 0.400-0.450 A/cm$^2$, 0.450-0.500 A/cm$^2$, 0.500-0.550 A/cm$^2$, 0.550-0.600 A/cm$^2$, 0.600-0.650 A/cm$^2$, 0.650-0.700 A/cm$^2$ or 0.650-0.750 A/cm$^2$.

Similarly, in case of other inner diameters, similar adjusting module can be provided for adjusting output power.

Inner diameter is 26-30 mm, and tube current density is selected to be 0.300-0.850 A/cm$^2$, wind speed is 1-5 m/s, and ultraviolet conversion efficiency η is greater than or equal to 30%. Moreover, in order to ensure ultraviolet conversion efficiency at ambient temperature of 10-35° C., tube current density is selected to be 0.330-0.800 A/cm$^2$. In addition, in order to ensure ultraviolet conversion efficiency when lamp power is adjusted, according to variation range of output power, tube current density is selected to be within 0.450-0.500 A/cm$^2$, 0.500-0.550 A/cm$^2$, 0.550-0.600 A/cm$^2$, 0.600-0.650 A/cm$^2$, 0.650-0.700 A/cm$^2$, 0.700-0.750 A/cm$^2$ or 0.750-0.800 A/cm$^2$.

Inner diameter is 20-26 mm, and tube current density is selected to be 0.300-1.100 A/cm$^2$, wind speed is 1-5 m/s, and ultraviolet conversion efficiency η is greater than or equal to 30%. Moreover, in order to ensure ultraviolet conversion efficiency at ambient temperature of 10-35° C., tube current density is selected to be 0.350-1.050 A/cm$^2$. In addition, in order to ensure ultraviolet conversion efficiency when lamp power is adjusted, according to variation range of output power, tube current density is selected to be within 0.450-0.500 A/cm$^2$, 0.500-0.550 A/cm$^2$, 0.550-0.600 A/cm$^2$, 0.600-0.650 A/cm$^2$, 0.650-0.700 A/cm$^2$, 0.700-0.750 A/cm$^2$ 0.750-0.800 A/cm$^2$, 0.800-0.850 A/cm$^2$, 0.850-0.900 A/cm$^2$, 0.900-0.950 A/cm$^2$, 0.950-1.000 A/cm$^2$ or 1.000-1.050 A/cm$^2$.

Inner diameter is 15-20 mm, and tube current density is selected to be 0.340-1.350 A/cm$^2$, wind speed is 1-5 m/s, and ultraviolet conversion efficiency η is greater than or equal to 30%. Moreover, in order to ensure ultraviolet conversion efficiency at ambient temperature of 10-35° C., tube current density is selected to be 0.400-1.300 A/cm$^2$. In addition, in order to ensure ultraviolet conversion efficiency when lamp power is adjusted, according to variation range of output power, tube current density is selected to be within 0.450-0.500 A/cm$^2$, 0.500-0.550 A/cm$^2$, 0.550-0.600 A/cm$^2$, 0.600-0.650 A/cm$^2$, 0.650-0.700 A/cm$^2$, 0.700-0.750 A/cm$^2$ 0.750-0.800 A/cm$^2$, 0.800-0.850 A/cm$^2$, 0.850-0.900 A/cm$^2$, 0.900-0.950 A/cm$^2$, 0.950-1.000 A/cm$^2$, 1.000-1.050 A/cm$^2$, 1.050-1.000 A/cm$^2$, 0.950-1.100 A/cm$^2$, 1.100-1.150 A/cm$^2$, 1.150-1.200 A/cm$^2$, 1.200-1.250 A/cm$^2$ or 1.250-1.300 A/cm$^2$.

Inner diameter is 12-15 mm, and tube current density is selected to be 0.335-1.000 A/cm$^2$, wind speed is 1-5 m/s, and ultraviolet conversion efficiency η is greater than or equal to 30%. Moreover, in order to ensure ultraviolet conversion efficiency at ambient temperature of 10-35° C., tube current density is selected to be 0.400-0.950 A/cm$^2$. In addition, in order to ensure ultraviolet conversion efficiency when lamp power is adjusted, according to variation range of output power, tube current density is selected to be within 0.450-0.500 A/cm$^2$, 0.500-0.550 A/cm$^2$, 0.550-0.600 A/cm$^2$, 0.600-0.650 A/cm$^2$, 0.650-0.700 A/cm$^2$, 0.700-0.750 A/cm$^2$ 0.750-0.800 A/cm$^2$, 0.800-0.850 A/cm$^2$, 0.850-0.900 A/cm$^2$ or 0.900-0.950 A/cm$^2$.

Inner diameter is 10-12 mm, and tube current density is selected to be 0.300-1.000 A/cm$^2$, wind speed is 1-5 m/s, and ultraviolet conversion efficiency η is greater than or equal to 30%. Moreover, in order to ensure ultraviolet conversion efficiency at ambient temperature of 10-35° C., tube current density is selected to be 0.350-0.950 A/cm$^2$. In addition, in order to ensure ultraviolet conversion efficiency when lamp power is adjusted, according to variation range of output power, tube current density is selected to be within 0.400-0.450 A/cm$^2$, 0.450-0.500 A/cm$^2$, 0.500-0.550 A/cm$^2$, 0.550-0.600 A/cm$^2$, 0.600-0.650 A/cm$^2$, 0.650-0.700 A/cm$^2$, 0.700-0.750 A/cm$^2$ 0.750-0.800 A/cm$^2$, 0.800-0.850 A/cm$^2$, 0.850-0.900 A/cm$^2$ or 0.900-0.950 A/cm$^2$.

Inner diameter is 8-10 mm, and tube current density is selected to be 0.300-0.900 A/cm$^2$, wind speed is 1-5 m/s, and ultraviolet conversion efficiency η is greater than or equal to 25%. Moreover, in order to ensure ultraviolet conversion efficiency at ambient temperature of 10-35° C., tube current density is selected to be 0.350-0.850 A/cm$^2$. In addition, in order to ensure ultraviolet conversion efficiency when lamp power is adjusted, according to variation range of output power, tube current density is selected to be within 0.400-0.450 A/cm$^2$, 0.450-0.500 A/cm$^2$, 0.500-0.550 A/cm$^2$, 0.550-0.600 A/cm$^2$, 0.600-0.650 A/cm$^2$, 0.650-0.700 A/cm$^2$, 0.700-0.750 A/cm$^2$, 0.750-0.800 A/cm$^2$ or 0.800-0.850 A/cm$^2$.

Inner diameter is 5-8 mm, and tube current density is selected to be 0.250-0.800 A/cm$^2$, wind speed is 1-5 m/s, and ultraviolet conversion efficiency η is greater than or equal to 25%. Moreover, in order to ensure ultraviolet conversion efficiency at ambient temperature of 10-35° C., tube current density is selected to be 0.300-0.750 A/cm$^2$. In addition, in order to ensure ultraviolet conversion efficiency when lamp power is adjusted, according to variation range of output power, tube current density is selected to be within 0.400-0.450 A/cm$^2$, 0.450-0.500 A/cm$^2$, 0.500-0.550 A/cm$^2$, 0.550-0.600 A/cm$^2$, 0.600-0.650 A/cm$^2$, 0.650-0.700 A/cm$^2$ or 0.700-0.750 A/cm$^2$.

Inner diameter is 3-5 mm, and tube current density is selected to be 0.280-0.900 A/cm$^2$, wind speed is 1-5 m/s, and ultraviolet conversion efficiency η is greater than or equal to 25%. Moreover, in order to ensure ultraviolet conversion efficiency at ambient temperature of 10-35° C., tube current density is selected to be 0.330-0.850 A/cm$^2$. In addition, in order to ensure ultraviolet conversion efficiency when lamp power is adjusted, according to variation range of output power, tube current density is selected to be within 0.400-0.450 A/cm$^2$, 0.450-0.500 A/cm$^2$, 0.500-0.550 A/cm$^2$, 0.550-0.600 A/cm$^2$, 0.600-0.650 A/cm$^2$, 0.650-0.700 A/cm$^2$ 0.700-0.750 A/cm$^2$, 0.750-0.800 A/cm$^2$ or 0.800-0.850 A/cm$^2$.

Thus, the present invention provides an ultraviolet sterilization and disinfection device, which has high ultraviolet conversion efficiency even when temperature and wind speed change and when output power is adjusted. In the ultraviolet sterilization and disinfection device, one or more low pressure ultraviolet lamps are provided, of which inner diameter is 30-36 mm and tube current density is 0.400-0.750 A/cm$^2$; inner diameter is 26-30 mm and tube current density is 0.450-0.800 A/cm$^2$; inner diameter is 20-26 mm and tube current density is 0.450-1.050 A/cm$^2$; inner diameter is 15-20 mm and tube current density is 0.450-1.350 A/cm$^2$; inner diameter is 12-15 mm and tube current density is 0.450-0.950 A/cm$^2$; inner diameter is 10-12 mm and tube current density is 0.400-0.950 A/cm$^2$; inner diameter is 8-10 mm and tube current density is 0.400-0.850 A/cm$^2$; inner diameter is 5-8 mm and tube current density is 0.400-0.750 A/cm$^2$; or inner diameter is 3-5 mm and tube current density is 0.400-0.850 A/cm$^2$. The selection of the above mentioned ranges are made to ensure ultraviolet conversion efficiency under various conditions like different sterilization and disinfection chamber volume, variations of temperature and wind speed, power adjustment and so on. When tube current density is too small, sterilization and disinfection chamber would have to be large and variation range of power adjustment is narrow. However, when tube current density is too large, ultraviolet conversion efficiency is low.

When an alloy containing bismuth, indium, tin and mercury or an alloy containing bismuth, plumbum, tin and mercury is used for mercury vapor pressure control, it would lead to better adaptation to the environment. That is, temperature can vary between 0-35° C., 0-45° C., 5-35° C., 5-45° C., 10-45° C., 10-55° C., 15-55° C., 15-60° C., 15-65° C., 15-70° C. or 15-75° C., and within these ranges, variation of ultraviolet output is less than 10% and variation of ultraviolet dosage of the gas flow is less than 10%.

Generally, the material used for mercury vapor pressure control within the low pressure ultraviolet lamp is liquid mercury. Alternatively, the material can be an alloy containing bismuth, indium, tin and mercury or an alloy containing bismuth, plumbum, tin and mercury.

Specifically, said liquid mercury is positioned in a discharge chamber of said low pressure ultraviolet lamp. Alternatively, the alloy containing bismuth, indium, tin and mercury or the alloy containing bismuth, plumbum, tin and mercury is positioned within a discharge pipe of said low pressure ultraviolet lamp, or fixed at a connection of said low pressure ultraviolet lamp where gas does not flow through.

Further, the ultraviolet sterilization and disinfection device according to the embodiment of the present invention may also comprise an adjusting module for adjusting ultraviolet dosage of the gas flow, by adjusting output power of low pressure ultraviolet lamp.

Further, lamp discharge arc length also has influence on conversion efficiency of ultraviolet irradiation with wavelength of 253.7 nm. Specifically, the shorter the arc length is, the lower the efficiency is. Specific settings of said low pressure ultraviolet lamp are as follows:

Inner diameter is 30-36 mm, discharge arc length of a single lamp may be larger than 80 cm, larger than 90 cm, larger than 100 cm, larger than 110 cm, larger than 120 cm, larger than 130 cm, larger than 140 cm, larger than 150 cm, larger than 160 cm, larger than 170 cm, larger than 180 cm, larger than 190 cm, or larger than 200 cm.

Inner diameter is 26-30 mm, discharge arc length of a single lamp may be larger than 80 cm, larger than 90 cm, larger than 100 cm, larger than 110 cm, larger than 120 cm, larger than 130 cm, larger than 140 cm, larger than 150 cm, larger than 160 cm, larger than 170 cm, larger than 180 cm, larger than 190 cm, or larger than 200 cm.

Inner diameter is 20-26 mm, discharge arc length of a single lamp may be larger than 80 cm, larger than 90 cm, larger than 100 cm, larger than 110 cm, larger than 120 cm, larger than 130 cm, larger than 140 cm, larger than 150 cm, larger than 160 cm, larger than 170 cm, larger than 180 cm, larger than 190 cm, or larger than 200 cm.

Inner diameter is 15-20 mm, discharge arc length of a single lamp may be larger than 60 cm, larger than 70 cm, larger than 80 cm, larger than 90 cm, larger than 100 cm, larger than 110 cm, larger than 120 cm, larger than 130 cm, larger than 140 cm, larger than 150 cm, larger than 160 cm, larger than 170 cm, larger than 180 cm, larger than 190 cm, or larger than 200 cm.

Inner diameter is 12-15 mm, discharge arc length of a single lamp may be larger than 60 cm, larger than 70 cm, larger than 80 cm, larger than 90 cm, larger than 100 cm, larger than 110 cm, larger than 120 cm, larger than 130 cm, larger than 140 cm, larger than 150 cm, larger than 160 cm, larger than 170 cm or larger than 180 cm.

Inner diameter is 8-10 mm, discharge arc length of a single lamp may be larger than 40 cm, larger than 50 cm, larger than 60 cm, larger than 70 cm, larger than 80 cm, larger than 90 cm, larger than 100 cm, larger than 110 cm, larger than 120 cm, larger than 130 cm, larger than 140 cm or larger than 150 cm.

Inner diameter is 5-8 mm, discharge arc length of a single lamp may be larger than 25 cm, larger than 30 cm, larger than 35 cm, larger than 40 cm, larger than 50 cm, larger than 60 cm, larger than 70 cm, larger than 80 cm, larger than 90 cm, larger than 100 cm, larger than 110 cm or larger than 120 cm.

Inner diameter is 3-5 mm, discharge arc length of a single lamp may be larger than 15 cm, larger than 18 cm, larger than 20 cm, larger than 25 cm, larger than 30 cm, larger than 35 cm, larger than 40 cm, larger than 50 cm, larger than 60 cm, larger than 70 cm or larger than 80 cm.

In another aspect, the present invention provides for a configuration method of an ultraviolet sterilization and disinfection device, comprising: optimization and design for tube diameter, tube current, discharge arc length, material for mercury vapor pressure control and filling gas for various low pressure ultraviolet lamps, and also optimization and design for parameters when ambient conditions like temperature and wind speed vary and output power is adjusted. The method further comprises:

providing one or more low pressure ultraviolet lamps in the ultraviolet sterilization and disinfection device;

further, providing one or more low pressure ultraviolet lamps in the ultraviolet sterilization and disinfection device comprises:

presetting initial positions of said low pressure ultraviolet lamps according to the structure of the sterilization and disinfection chamber said ultraviolet sterilization and disinfection device;

dividing ultraviolet irradiation area of said low pressure ultraviolet lamps into discrete grids, summing average illuminance value at initial position of each grid, calculating ultraviolet illuminance uniformity across said ultraviolet irradiation area, and adjusting the position of said low pressure ultraviolet lamps according to the ultraviolet illuminance uniformity so that the ultraviolet illuminance uniformity meets design requirements;

and determining dimension, structure and tube current density of each of said low pressure ultraviolet lamps after position adjustment, according to preset ultraviolet dosage.

In the step of adjusting the position of said low pressure ultraviolet lamps according to the ultraviolet illuminance uniformity, ANSYS or similar fluid analysis software is used to analyze flow field of the gas flow, so that the flow field is distributed uniformly.

Further, preset average illuminance value of each conjunction within said discrete grids can be obtained using the equation as follows:

$$E = \frac{P(2\alpha + \sin 2\alpha)}{2\pi^2 DL},$$

wherein, E represents ultraviolet intensity, P represents ultraviolet power, α represents half the angle between the conjunction of which ultraviolet intensity is to be calculated and arc length of ultraviolet lamp, L represents discharge arc length of ultraviolet lamp and D represents normal distance between ultraviolet lamp and the conjunction of which ultraviolet intensity is to be calculated.

In the embodiment of the present invention, sterilization and disinfection efficiency of low pressure ultraviolet lamp can be greatly enhanced by proper design of inner diameter and tube current density of low pressure ultraviolet lamp. On the other hand, the shape of ultraviolet irradiation area is simplified, and specific conjunctions where ultraviolet sterilization and disinfection lamps are positioned and corresponding sterilization and disinfection intensities can be obtained via by reusing discrete and integration calculations. As the influence of each lamp on the calculated conjunction is considered, ultraviolet intensities at different locations are designed in a more reasonable way, so that ultraviolet illuminance of sterilization and disinfection lamps in the device is uniform and thus sterilization and disinfection efficiency is enhanced.

Figure 2:
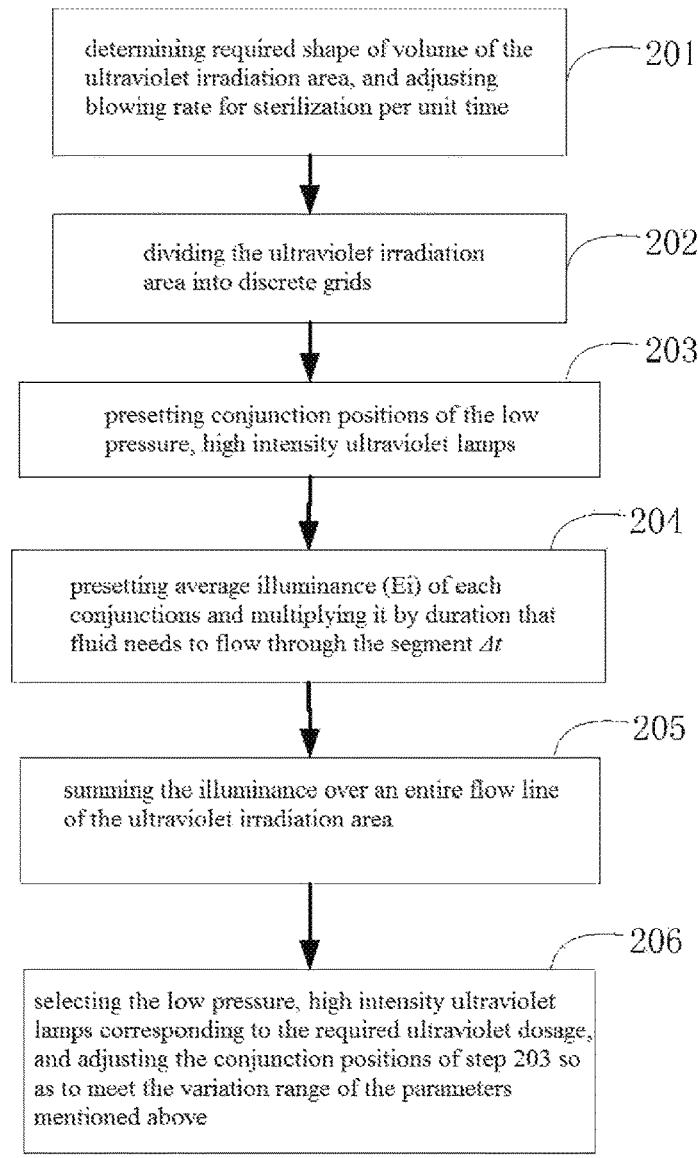
FIG. 2 is another embodiment of the configuration method of an ultraviolet sterilization and disinfection device according to the present invention.
Figure 3:
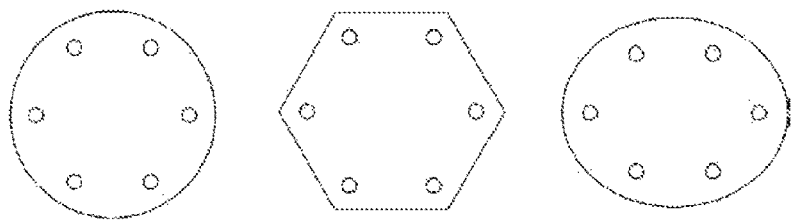
FIG. 3 is a schematic sectional view of three different shaped sterilization and disinfection chambers according to the present invention.

What is shown in FIG. 1 is a specific embodiment of configuration method of ultraviolet sterilization and disinfection device according to the present invention. The method is mainly used for setting the positions of ultraviolet sterilization and disinfection lamps in the ultraviolet sterilization and disinfection device, the ultraviolet sterilization and disinfection lamp comprising a discharge device, a discharge vessel and amalgam filled in the discharge vessel. The method comprises the following steps:

101. based on the properties of the ultraviolet sterilization and disinfection device, determining required shape and volume of ultraviolet irradiation area and blowing rate for sterilization and disinfection per unit time;

102. dividing the ultraviolet irradiation area into discrete grids according to its cross section;

103. presetting positions of each conjunction of the discrete grids, average illuminance and duration that air flows through the ultraviolet irradiation area, according to the required shape and volume of ultraviolet irradiation area and blowing rate for sterilization and disinfection per unit time;

wherein, preset average illuminance value of each conjunction within said discrete grids can be obtained using the equation as follows:

$$E = \frac{P(2\alpha + \sin 2\alpha)}{2\pi^2 DL},$$

wherein, E represents ultraviolet intensity, P represents ultraviolet power, α represents half the angle between the conjunction of which ultraviolet intensity is to be calculated and arc length of ultraviolet lamp, L represents discharge arc length of ultraviolet lamp and D represents normal distance between ultraviolet lamp and the conjunction of which ultraviolet intensity is to be calculated;

the average illuminance Ei of two vertically adjacent points is taken as the illuminance of the discrete segment;

104. summing all of the illuminance of each flow line of the ultraviolet irradiation area according to the average illuminance of each conjunction and duration that air flows through the ultraviolet irradiation area, so as to obtain the ultraviolet dosage that air flows through all the flow lines of the ultraviolet irradiation area;

this step may further comprises: calculating the ultraviolet dosage uniformity of the ultraviolet irradiation area, and adjusting the positions of each conjunction of the discrete grids, average illuminance and duration that air flows through the ultraviolet irradiation area of step 103 according to the ultraviolet dosage uniformity and an expected ultraviolet dosage uniformity, until the ultraviolet dosage uniformity calculated reaches the expected one;

105. determining the ultraviolet dosage of the ultraviolet sterilization and disinfection lamps according to the ultraviolet dosage of each flow line, and determining the arrangement of each of the ultraviolet sterilization and disinfection lamps according to the position of each of the conjunctions of the discrete grids;

Technical details of the present invention are further explained below by specific embodiments. In FIG. 2, another specific embodiment of configuration method of the ultraviolet sterilization and disinfection device according to the present invention is shown, the method comprising:

201. determining required shape of volume of the ultraviolet irradiation area, and adjusting blowing rate for sterilization and disinfection per unit time. It is assumed that the sectional area of the ultraviolet irradiation area is S, the height of the ultraviolet irradiation area is H, the blowing rate per hour is Q, and then the duration t that air flows through the ultraviolet irradiation area can be determined, i.e. t=H/(Q/S). In case that the duration is known, the required ultraviolet illuminance can be backwardly worked out, according to different known dosage requirement of each bacterium, virus and other microorganism. In FIG. 3, sections of sterilization and disinfection chambers having different shapes are shown.

Figure 4:
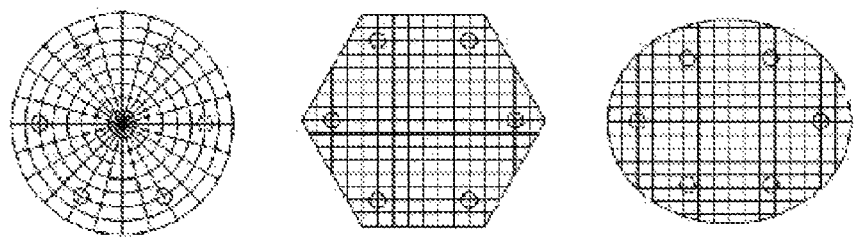
FIG. 4 is a schematic view of the three different shaped sections of FIG. 3 which are divided into discrete grids.

202. dividing the ultraviolet irradiation area into discrete grids. That is, when the required ultraviolet illuminance is known, one or more low pressure, high intensity ultraviolet lamps corresponding to the ultraviolet dosage are selected, and are arranged in the area in an equally spaced manner. Differential and discrete calculations are carried out based on the distribution conditions and areas of the lamps, so as to obtain an optimal arrangement. In FIG. 4, schematic illustration of dividing the differently shaped sections of FIG. 3 into discrete grids.

203. presetting conjunction positions of the low pressure, high intensity ultraviolet lamps. In FIGS. 3 and 4, the small circles are schematic illustration of conjunction positions of ultraviolet irradiation areas having different shapes.

Figure 5:
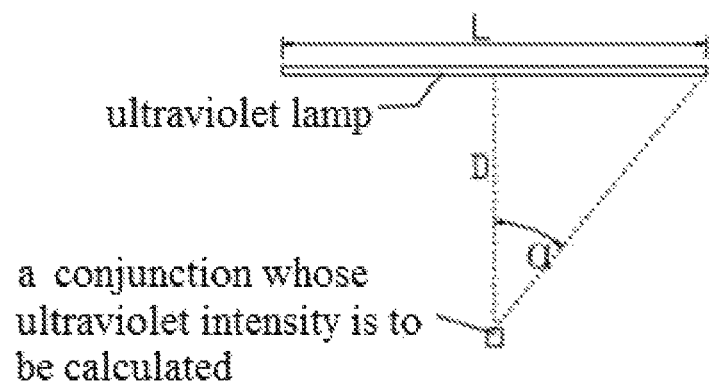
FIG. 5 is a schematic view illustrating the meaning of α, L and D according to the present invention.

204. presetting average illuminance (Ei) of each conjunctions. Ei can be obtained by the following equation. That is, for each of the discrete conjunctions, illuminance calculation can be carried out by the following variation of Keitz equation:

$$E = \frac{P(2\alpha + \sin 2\alpha)}{2\pi^2 DL},$$

wherein, P represents the ultraviolet throughput of the ultraviolet lamps, specifically, $P=P_1 \times \eta = I \times V \times \alpha 1 \times \eta$, and wherein V represents the voltage applied, I represents discharge current, (I equals to tube current density (A/cm$^2$) multiplying tube axial sectional area (cm$^2$), and the tube axial sectional area equals to $\pi$ multiplying (tube diameter/2)$^2$); and the voltage V equals to $V_{AK}$ adding to e*Lc, and wherein $V_{AK}$ represents potential drop of the electrode and is generally 17V, e represents intensity of axial electrical field of the positive column district, Lc represents the length of discharging positive column district. The voltage applied is generally 40-70% of the supplied voltage depending on different voltages supplied. $\alpha 1$ represents distortion coefficient of the lamp, and $\eta$ represents ultraviolet conversion efficiency, i.e. the fraction of the electric power supplied to the ultraviolet lamp that converted into ultraviolet throughput (power). $\alpha$ represents half the angle between the conjunction of which ultraviolet intensity is to be calculated and arc length of ultraviolet lamp, L represents discharge arc length of ultraviolet lamp and D represents normal distance between ultraviolet lamp and the conjunction of which ultraviolet intensity is to be calculated. In FIG. 5, the meaning of $\alpha$, L and D is schematically illustrated.

The average illuminance Ei of two vertically adjacent points is taken as the illuminance of the discrete segment.

It can be seen, the calculation of illuminance of each conjunction has taken into account the influence of each lamp. The more the discrete grids are, the more the conjunctions are, the more the calculation work is, and yet the higher the precision is.

205. summing the illuminance over an entire flow line of the ultraviolet irradiation area; further calculating ultraviolet dosage uniformity of the ultraviolet irradiation area, comparing it with the expected one and adjusting the preset parameters of step 204 to meet the expected ultraviolet dosage uniformity.

Specifically, the average illuminance of the discrete segment obtained in the steps above is multiplied by duration that fluid needs to flow through the segment (Ei*$\Delta$t), i.e. the illuminance of an entire flow line of the ultraviolet irradiation area is summed. Illuminance of other flow lines is calculated in the same way, and illuminance of different flow lines is obtained. What is obtained is the ultraviolet dosage that bacteria would be exposed to when passing the ultraviolet irradiation area.

206. selecting the low pressure, high intensity ultraviolet lamps corresponding to the required ultraviolet dosage, and adjusting the conjunction positions of step 203 so as to meet the variation range of the parameters mentioned above. Further, ultraviolet dosage uniformity of the ultraviolet sterilization and disinfection area can be calculated and compared with the preset value, and then conjunction positions of step 203 can be adjusted so as to meet the expected ultraviolet dosage uniformity.

Distribution of dosage uniformity is calculated according to the following equation:

$$\text{dosage uniformity} = \frac{\text{DOSE(min)}}{\text{DOSE(max)}} \times 100\%$$

When the rotation speed is at 1300 rpm, the minimum dosage is present in vicinity to tube wall and the value is 6414 uws/cm$^2$, and the maximum dosage is present in the middle part about 5 mm away from the two sides and the value is 8598 uws/cm$^2$. The calculated dosage uniformity is 75%.

It can be seen from the description above that, in the embodiment of the present invention, the shape of the ultraviolet irradiation area is simplified, and then specific conjunction positions for setting ultraviolet sterilization and disinfection lamps and corresponding ultraviolet sterilization and disinfection intensity of each conjunction are obtained by reusing discrete and integration calculations. The calculation has taken into account the influence of each lamp, so that intensity settings of ultraviolet sterilization and disinfection lamps at different positions are made more reasonable and the illuminance of ultraviolet sterilization and disinfection lamps within the entire apparatus is more uniform. Thus ultraviolet sterilization and disinfection efficiency is enhanced.

The so-designed ultraviolet sterilization and disinfection device comprises ultraviolet sterilization and disinfection lamps, a blower, an air inlet, a sterilization and disinfection chamber, and an air outlet, the sterilization and disinfection chamber comprising a sterilization and disinfection module having at least one ultraviolet module, the ultraviolet module using the low pressure ultraviolet lamps optimized above, wherein ultraviolet illuminance and flow field are suitably designed.

In addition to the ultraviolet module, the sterilization and disinfection module further comprises photocatalyst, electrostatic module, filter module and ozone module.

The ultraviolet sterilization and disinfection further comprises light shielding guide plate, the light shielding guide plate being in the form of grids, each of the grids comprising a curved light shielding guide portion and a straight guide portion being straight at least in part along the direction in which air flows towards the air outlet.

The light shielding guide plate is made of metal plate, and various voltages are applied spaced on the light shielding guide plate so that the light shielding guide plate serves the function of being electrostatic.

The sterilization and disinfection module comprises at least one detachable insertion structure, or the ultraviolet module, photocatalyst module, electrostatic module, filter module and ozone module can be the detachable insertion structure. The sterilization and disinfection module can be mounted/dismounted separately, or a number of sterilization and disinfection modules are connected by a connection and thus can be mounted/dismounted as a whole.

Specifically, the detachable insertion structure of the sterilization and disinfection module is inserted directly into a groove prefabricated in the ultraviolet sterilization and disinfection device;

Specifically, the detachable insertion structure of the sterilization and disinfection module is connected to the ultraviolet sterilization and disinfection device by movable structures like spring snap, clip snap, etc.

Specifically, the detachable insertion structure of the sterilization and disinfection module is pressed against onto the ultraviolet sterilization and disinfection device by screws or a housing.

Figure 6:
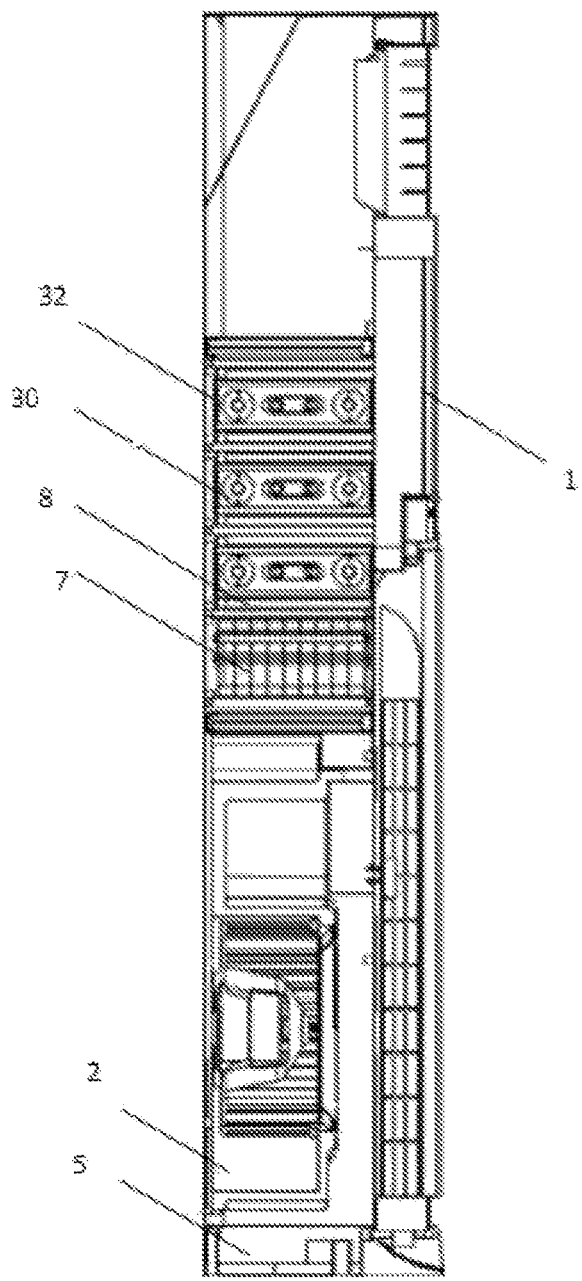
FIG. 6 is a schematic view of the configuration of an ultraviolet sterilization and disinfection device according to the present invention.

FIG. 6 shows schematic structural view of the ultraviolet sterilization device. The ultraviolet sterilization device comprises a plurality of ultraviolet sterilization modules 30 and a frame 32 for fixing the ultraviolet sterilization modules, each of the ultraviolet sterilization modules comprising one or more ultraviolet sterilization lamps, the frame comprising a detachable insertion structure for accommodating and fixing the one or more ultraviolet sterilization modules. That is, the ultraviolet sterilization modules within the ultraviolet sterilization device are replaceable modules. When a sterilization lamp within the ultraviolet sterilization device is failed, it can be replaced or repaired separately. On the other hand, depending on actual needs, it is possible to achieve adjustment of ultraviolet illuminance when required, by increasing or reducing the number of ultraviolet sterilization modules. When a ultraviolet sterilization module is removed, a frame may be positioned in this place, where no ultraviolet sterilization lamp is present. The added frame serves to hold the device and prevent leakage of ultraviolet irradiation and air. Alternatively, a photocatalyst module can be added here, enhancing the ability of removing organic matters. In this figure, reference numeral 1 represents for a housing, reference numeral 2 represents for an air intake passage, and reference numeral 5 represents for a support base.

In addition, the ultraviolet sterilization and disinfection device shown in FIG. 6 further comprises a photocatalyst module 8 positioned in the housing for removing smell and other organic pollution matters, and also for killing bacteria and viruses. The photocatalyst of the present embodiment comprises a sheet material or netting material containing a photocatalyst material and positioned at two ends of a disinfection chamber of the sterilization and disinfection device, the photocatalyst material comprising one or more of nano titanium oxide, nano zinc oxide and nano silver. When the sterilization and disinfection device comprises a plurality of sterilization and disinfection modules, the photocatalyst comprises photocatalyst sheet materials or netting materials positioned at two ends of each sterilization and disinfection module.

In addition, the ultraviolet sterilization and disinfection device shown in FIG. 6 further comprises an electrostatic device 7 positioned in the housing, for removing solid particles and for absorbing and removing bacteria and viruses. The electrostatic device of the present embodiment is positioned at the front end of the sterilization and disinfection module, and can also be positioned at the rear end thereof depending actual needs.

As examples, specifications of the ultraviolet sterilization and disinfection device designed in the manner stated above are described below.

For a rectangular sterilization and disinfection chamber, the length, the width and the height are 30 cm, 20 cm and 40 cm, respectively. Three M type ultraviolet sterilization and disinfection lamps are used in parallel, center distances between the planes of the three lamps being 15 cm, the outer diameter of the lamps being 15 mm, and the output power being 120 W. Velocity of air stream within the sterilization and disinfection chamber is 1.2 m/s. Minimum illuminance is 27 mW/cm$^2$, minimum ultraviolet dosage is 9.0 mJ/cm$^2$ and flow rate is 0.072 m$^3$/s. In order to reach the reference dosage of 5 mJ/cm$^2$, the ratio of the volume of the ultraviolet sterilization and disinfection chamber to flow rate per second is $(0.3*0.2*0.4)*5/(0.072*9.0)=0.185$. In case that the reference flow rate is 10 m$^3$/h (0.0278 m$^3$/s), the required ultraviolet power is $(3*120*10*0.00278)/(0.0720*9)=15.4$ W.

For a cylindrical sterilization and disinfection chamber, the diameter is 40 cm and the height is 60 cm. Four circular type ultraviolet sterilization and disinfection lamps are used in parallel, center distances between the planes of the three lamps being 15 cm, the outer diameter of the lamps being 19 mm, and the output power being 250 W. Velocity of air stream within the sterilization and disinfection chamber is 2.0 m/s. Minimum illuminance is 25 mW/cm$^2$, minimum ultraviolet dosage is 7.5 mJ/cm$^2$ and flow rate is 0.25 m$^3$/s. In order to reach the reference dosage of 5 mJ/cm$^2$, the ratio of the volume of the ultraviolet sterilization and disinfection chamber to flow rate per second is 0.20. In case that the reference flow rate is 10 m$^3$/h, the required ultraviolet power is 14.8 W.

For a rectangular sterilization and disinfection chamber used for central air-conditioners, the height, the width and the length are 60 cm, 60 cm and 190 cm, respectively. Nine straight type ultraviolet sterilization and disinfection lamps are arranged in parallel along the length direction in three lines, three lamps in each line. Seen from the sectional plane taken along the plane spanned by the width direction and the height direction, the nine lamps are arranged in a shape of square, one of the lamps being positioned in the center of the square shape. The square is 10 cm away from the end surface of the sterilization and disinfection chamber, either along the width direction or along the height direction. The outer diameter of the lamps is 38 mm, the output power is 800 W and thus the overall power is 7200 W. Velocity of air stream within the sterilization and disinfection chamber is 3.0 m/s. The inner wall of the sterilization and disinfection chamber is coated with a layer of polished aluminum. Minimum illuminance is 20 mW/cm$^2$, minimum ultraviolet dosage is 12.7 mJ/cm$^2$ and flow rate is 1.08 m$^3$/s. In order to reach the reference dosage of 5 mJ/cm$^2$, the ratio of the volume of the ultraviolet sterilization and disinfection chamber to flow rate per second is 0.249. In case that the reference flow rate is 10 m$^3$/h, the required ultraviolet power is 14.6 W. When the rectangular sterilization and disinfection chamber serves for electrostatic dedusting, it is able to remove particles and dusts with a size of below 10 μm. The function of dedusting can be realized daily, weekly or monthly, automatically or manually. Aggregated dusts are free of germs and viruses, and are absorbed into small dust collection box and then treated safely and conveniently.

For another cylindrical sterilization and disinfection chamber, the diameter is 60 cm and the height is 70 cm. Four circular type electrodeless ultraviolet sterilization and disinfection lamps are used in parallel, center distances between the planes of the three lamps being 18 cm, the outer diameter of the lamps being 38 mm, and the output power being 700 W. The electrodeless ultraviolet sterilization and disinfection lamps are in the form of insertion pipes. Velocity of air stream within the sterilization and disinfection chamber is 2.0 m/s. The inner wall of the sterilization and disinfection chamber is coated with a layer of polished aluminum. Minimum illuminance is 22 mW/cm$^2$, minimum ultraviolet dosage is 7.7 mJ/cm$^2$ and flow rate is 0.565 m$^3$/s. In order to reach the reference dosage of 5 mJ/cm$^2$, the ratio of the volume of the ultraviolet sterilization and disinfection chamber to flow rate per second is 0.23. In case that the reference flow rate is 10 m$^3$/h, the required ultraviolet power is 15.8 W.

The embodiments described above are preferred embodiments of the present invention. It is to be noted that, a variety of developments and modifications can be made by one skilled in the art without departing from the concept of the present invention, these developments and modifications falling within the protection scope of the present invention.

What is claimed is:

1. An ultraviolet sterilization and disinfection device, wherein in order that an ultraviolet dosage of the ultraviolet sterilization and disinfection device reaches a reference dosage of 5 mJ/cm$^2$, a ratio of a volume of an ultraviolet sterilization and disinfection chamber of the ultraviolet sterilization and disinfection device to a flow rate per second is less than 0.8; at a reference flow rate of 10 m³/h, an output power of lamps required to reach the reference dosage of 5 mJ/cm² is less than 22.0 W; a wind speed of the ultraviolet sterilization and disinfection device is 1-5 m/s, and the ultraviolet sterilization and disinfection device comprises one or more low pressure ultraviolet lamps, for the low pressure ultraviolet lamps,
- an inner diameter being 30-36 mm and a tube current density being 0.250-0.800 A/cm²; or
- an inner diameter being 26-30 mm and a tube current density being 0.280-0.850 A/cm²; or
- an inner diameter being 20-26 mm and a tube current density being 0.300-1.100 A/cm²; or
- an inner diameter being 15-20 mm and a tube current density being 0.340-1.350 A/cm²; or
- an inner diameter being 12-15 mm and a tube current density being 0.335-1.000 A/cm²; or
- an inner diameter being 10-12 mm and a tube current density being 0.300-1.000 A/cm²; or
- an inner diameter being 8-10 mm and a tube current density being 0.300-0.900 A/cm²; or
- an inner diameter being 5-8 mm and a tube current density being 0.250-0.800 A/cm²; or
- an inner diameter being 3-5 mm and a tube current density being 0.280-0.900 A/cm2;
- a material in the low pressure ultraviolet lamps used for mercury vapor pressure control is liquid mercury; or a material in the low pressure ultraviolet lamps used for mercury vapor pressure control is an alloy containing bismuth, indium, tin, and mercury or an alloy containing bismuth, plumbum, tin, and mercury.

2. The ultraviolet sterilization and disinfection device as claimed in claim 1, wherein the low pressure ultraviolet lamps are electrode-containing low pressure ultraviolet lamps or electrodeless low pressure ultraviolet lamps.

3. The ultraviolet sterilization and disinfection device as claimed in claim 2, wherein the electrode-containing low pressure ultraviolet lamps are of a U shape, a Π shape, an Π shape, a double U shape, a double Π shape, a double Π shape, a triple U shape, a triple Π shape, a triple Π shape, a quadric U shape, a quadric Π shape, a quadric Π shape, a W shape, an M shape, a U-H connection shape, or a Π-H connection shape.

4. The ultraviolet sterilization and disinfection device as claimed in claim 2, wherein the electrodeless low pressure ultraviolet lamps are of a ring shape, a rectangular shape, a square shape, an oval shape, or other closed-loop shapes.

5. The ultraviolet sterilization and disinfection device as claimed in claim 1, wherein when the wind speed of the ultraviolet sterilization and disinfection device is 1-5 m/s, the low pressure ultraviolet lamps are set as follows:
- the inner diameter is 30-36 mm, the tube current density is selected to be within 0.400-0.450 A/cm², 0.450-0.500 A/cm², 0.500-0.550 A/cm², 0.550-0.600 A/cm², 0.600-0.650 A/cm², 0.650-0.700 A/cm², or 0.650-0.750 A/cm², and the ultraviolet conversion efficiency η is greater than or equal to 30%; or
- the inner diameter is 26-30 mm, the tube current density is selected to be within 0.450-0.500 A/cm², 0.500-0.550 A/cm², 0.550-0.600 A/cm², 0.600-0.650 A/cm², 0.650-0.700 A/cm², 0.700-0.750 A/cm², or 0.750-0.800 A/cm², and ultraviolet conversion efficiency η is greater than or equal to 30%; or
- the inner diameter is 20-26 mm, the tube current density is selected to be within 0.450-0.500 A/cm², 0.500-0.550 A/cm², 0.550-0.600 A/cm², 0.600-0.650 A/cm², 0.650-0.700 A/cm², 0.700-0.750 A/cm², 0.750-0.800 A/cm², 0.800-0.850 A/cm², 0.850-0.900 A/cm², 0.900-0.950 A/cm², 0.950-1.000 A/cm², or 1.000-1.050 A/cm², and ultraviolet conversion efficiency η is greater than or equal to 30%; or
- the inner diameter is 15-20 mm, the tube current density is selected to be within 0.450-0.500 A/cm², 0.500-0.550 A/cm², 0.550-0.600 A/cm², 0.600-0.650 A/cm², 0.650-0.700 A/cm², 0.700-0.750 A/cm², 0.750-0.800 A/cm², 0.800-0.850 A/cm², 0.850-0.900 A/cm², 0.900-0.950 A/cm², 0.950-1.000 A/cm², 1.000-1.050 A/cm², 1.050-1.000 A/cm², 0.950-1.100 A/cm², 1.100-1.150 A/cm², 1.150-1.200 A/cm², 1.200-1.250 A/cm² or 1.250-1.300 A/cm², and ultraviolet conversion efficiency η is greater than or equal to 30%; or
- the inner diameter is 12-15 mm, the tube current density is selected to be within 0.450-0.500 A/cm², 0.500-0.550 A/cm², 0.550-0.600 A/cm², 0.600-0.650 A/cm², 0.650-0.700 A/cm², 0.700-0.750 A/cm², 0.750-0.800 A/cm², 0.800-0.850 A/cm², 0.850-0.900 A/cm², or 0.900-0.950 A/cm², and ultraviolet conversion efficiency η is greater than or equal to 30%; or
- the inner diameter is 10-12 mm, the tube current density is selected to be within 0.400-0.450 A/cm², 0.450-0.500 A/cm², 0.500-0.550 A/cm², 0.550-0.600 A/cm², 0.600-0.650 A/cm², 0.650-0.700 A/cm², 0.700-0.750 A/cm², 0.750-0.800 A/cm², 0.800-0.850 A/cm², 0.850-0.900 A/cm², or 0.900-0.950 A/cm², and ultraviolet conversion efficiency η is greater than or equal to 30%; or
- the inner diameter is 8-10 mm, the tube current density is selected to be within 0.400-0.450 A/cm², 0.450-0.500 A/cm², 0.500-0.550 A/cm², 0.550-0.600 A/cm², 0.600-0.650 A/cm², 0.650-0.700 A/cm², 0.700-0.750 A/cm², 0.750-0.800 A/cm² or 0.800-0.850 A/cm², and ultraviolet conversion efficiency η is greater than or equal to 25%; or
- the inner diameter is 5-8 mm, the tube current density is selected to be within 0.400-0.450 A/cm², 0.450-0.500 A/cm², 0.500-0.550 A/cm², 0.550-0.600 A/cm², 0.600-0.650 A/cm², 0.650-0.700 A/cm², or 0.700-0.750 A/cm², and ultraviolet conversion efficiency η is greater than or equal to 25%; or
- the inner diameter is 3-5 mm, the tube current density is selected to be within 0.400-0.450 A/cm², 0.450-0.500 A/cm², 0.500-0.550 A/cm², 0.550-0.600 A/cm², 0.600-0.650 A/cm², 0.650-0.700 A/cm², 0.700-0.750 A/cm², 0.750-0.800 A/cm², or 0.800-0.850 A/cm², and ultraviolet conversion efficiency η is greater than or equal to 25%.

6. The ultraviolet sterilization and disinfection device as claimed in claim 1, wherein ultraviolet sterilization and disinfection device further comprises an adjusting module for adjusting an ultraviolet dosage of the gas flow, by adjusting an output power of the low pressure ultraviolet lamps.

7. The ultraviolet sterilization and disinfection device as claimed in claim 1, wherein the low pressure ultraviolet lamps are set as follows:
- the inner diameter is 30-36 mm, and the discharge arc length of a single lamp is larger than 80 cm; or
- the inner diameter is 26-30 mm, and a discharge arc length of a single lamp is larger than 80 cm; or
- the inner diameter is 20-26 mm, and a discharge arc length of a single lamp is larger than 80 cm; or
- the inner diameter is 15-20 mm, and a discharge arc length of a single lamp is larger than 60 cm; or the inner diameter is 12-15 mm, and a discharge arc length of a single lamp is larger than 60 cm; or the inner diameter is 8-10 mm, and a discharge arc length of a single lamp is larger than 40 cm; or the inner diameter is 5-8 mm, and a discharge arc length of a single lamp is larger than 25 cm; or the inner diameter is 3-5 mm, and a discharge arc length of a single lamp is larger than 15 cm.

8. The ultraviolet sterilization and disinfection device as claimed in claim 1, wherein the liquid mercury is positioned within a discharging chamber of the low pressure ultraviolet lamps.

9. The ultraviolet sterilization and disinfection device as claimed in claim 8, wherein the alloy containing bismuth, indium, tin, and mercury or the alloy containing bismuth, plumbum, tin, and mercury is positioned at an exhaust pipe of the low pressure ultraviolet lamps or connections of the low pressure ultraviolet lamps where a gas does not flow through.

10. The ultraviolet sterilization and disinfection device as claimed in claim 8, wherein when a temperature at an exhaust pipe of the low pressure ultraviolet lamps or connections of the low pressure ultraviolet lamps where a gas does not flow through is within the ranges of 75-95° C., 85-105° C., or 95-135° C., it is the alloy containing bismuth, indium, tin, and mercury that is positioned within the low pressure ultraviolet lamps for mercury vapor pressure control.

11. The ultraviolet sterilization and disinfection device as claimed in claim 8, wherein when a temperature at an exhaust pipe of the low pressure ultraviolet lamps or connections of the low pressure ultraviolet lamps where gas does not flow through is within the ranges of 60-90° C., 65-95° C., 65-105° C., or 70-115° C., it is the alloy containing bismuth, plumbum, tin, and mercury that is positioned within the low pressure ultraviolet lamps for mercury vapor pressure control.

12. An ultraviolet sterilization and disinfection device, wherein ultraviolet sterilization and disinfection device comprises the one or more low pressure ultraviolet lamps according to claim 1, a blower, an air inlet, a sterilization and disinfection chamber, and an air outlet, the sterilization and disinfection chamber comprising a sterilization and disinfection module having at least one ultraviolet module.

13. The ultraviolet sterilization and disinfection device as claimed in claim 12, wherein the sterilization and disinfection module further comprises one or more of a photocatalyst, an electrostatic module, a filter module, and an ozone module.

14. The ultraviolet sterilization and disinfection device as claimed in claim 12, wherein ultraviolet sterilization and disinfection device further comprises a light shielding guide plate, the light shielding guide plate being in the form of grids.

15. The ultraviolet sterilization and disinfection device as claimed in claim 14, wherein each of the grids comprises a curved light shielding guide portion and a straight guide portion which is straight at least in part along a direction in which air flows towards the air outlet.

16. The ultraviolet sterilization and disinfection device as claimed in claim 14, wherein the light shielding guide plate is made from a metal plate, and various voltages are applied in a spaced manner on the light shielding guide plate so that the light shielding guide plate serves the function of being electrostatic.

17. The ultraviolet sterilization and disinfection device as claimed in claim 12, wherein the sterilization and disinfection module comprises a detachable insertion structure.

18. The ultraviolet sterilization and disinfection device as claimed in claim 17, wherein the detachable insertion structure can be mounted/dismounted separately, or a number of the sterilization and disinfection modules are connected by a connection and thus can be mounted/dismounted as a whole.

19. The ultraviolet sterilization and disinfection device as claimed in claim 17, wherein the detachable insertion structure is inserted directly into a groove prefabricated in ultraviolet sterilization and disinfection device; or the detachable insertion structure is connected to ultraviolet sterilization and disinfection device by a movable structure; or the detachable insertion structure is pressed against the ultraviolet sterilization and disinfection device by screws or a housing.

20. The ultraviolet sterilization and disinfection device as claimed in claim 19, wherein the movable structure includes at least one selected from a spring snap and a clip snap.

\* \* \* \* \*